(12) United States Patent
Makansi

(10) Patent No.: US 11,504,543 B2
(45) Date of Patent: Nov. 22, 2022

(54) WIRELESS NEURAL STIMULATOR WITH INJECTABLE

(71) Applicant: StimAire, Inc., Tucson, AZ (US)

(72) Inventor: Tarek Makansi, Tucson, AZ (US)

(73) Assignee: STIMAIRE, INC., Tucson, AZ (US)

( * ) Notice: Subject to any disclaimer, the term of this patent is extended or adjusted under 35 U.S.C. 154(b) by 85 days.

(21) Appl. No.: 16/961,645

(22) PCT Filed: Jan. 14, 2019

(86) PCT No.: PCT/US2019/013538
§ 371 (c)(1),
(2) Date: Jul. 10, 2020

(87) PCT Pub. No.: WO2019/140404
PCT Pub. Date: Jul. 18, 2019

(65) Prior Publication Data
US 2020/0338358 A1 Oct. 29, 2020

Related U.S. Application Data

(60) Provisional application No. 62/750,326, filed on Oct. 25, 2018, provisional application No. 62/716,656, filed on Aug. 9, 2018, provisional application No. 62/685,860, filed on Jun. 15, 2018, provisional application No. 62/617,241, filed on Jan. 14, 2018.

(51) Int. Cl.
*A61N 2/00* (2006.01)
*A61N 1/05* (2006.01)
*A61N 2/02* (2006.01)

(52) U.S. Cl.
CPC ........... *A61N 2/006* (2013.01); *A61N 1/0551* (2013.01); *A61N 2/02* (2013.01)

(58) Field of Classification Search
CPC .... A61N 1/0529; A61N 1/08; A61N 1/36057; A61N 1/36078; A61N 1/36125; A61N 1/37514; A61N 1/3756; A61N 1/3787; A61N 2/006; A61N 2/02
See application file for complete search history.

(56) References Cited

U.S. PATENT DOCUMENTS 6,174,276 B1    1/2001  Blackwell
7,904,171 B2    3/2011  Parramon et al.
(Continued)

FOREIGN PATENT DOCUMENTS

WO    2012013201 A1    2/2012
WO    2018071906 A1    4/2018

OTHER PUBLICATIONS

International Search Report and Written Opinion dated Apr. 12, 2019 for PCT Application No. PCT/US2019/013538, 22 pages.
(Continued)

*Primary Examiner* — Christine H Matthews
(74) *Attorney, Agent, or Firm* — Dorsey & Whitney LLP

(57) ABSTRACT

Neural stimulator systems with an external magnetic coil to produce changing magnetic fields is applied outside the body, in conjunction with one or more tiny injectable objects that concentrates the induced electric or magnetic field to a highly-targeted location. These systems include a driver circuit for the magnetic coil that allows for high voltage and fast pulses in the coil, while requiring low-voltage power supply that may be powered by a wearable or portable external device, along with the coil and driver circuit.

14 Claims, 28 Drawing Sheets

(56) References Cited

U.S. PATENT DOCUMENTS

| | | |
|---|---|---|
| 8,165,692 B2 | 4/2012 | Strother et al. |
| 8,718,783 B2 | 5/2014 | Bolea et al. |
| 9,526,906 B2 | 12/2016 | Mashiach |
| 2015/0148878 A1 | 5/2015 | Yoo et al. |
| 2015/0306384 A1 | 10/2015 | Denk et al. |
| 2016/0228713 A1 | 8/2016 | Bar-cohen et al. |

OTHER PUBLICATIONS

Extended European Search Report received in EP App No. 19738649.3 dated Sep. 10, 2021.

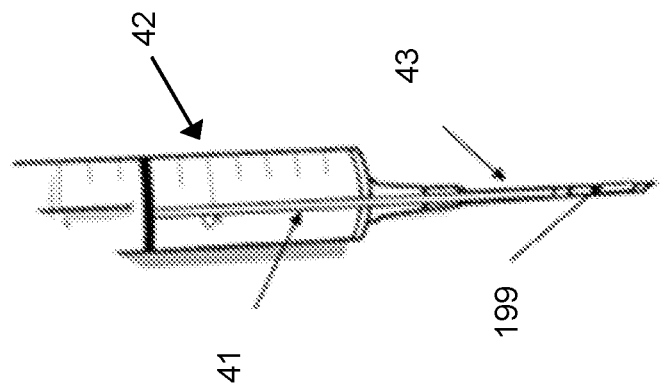
FIG. 2b
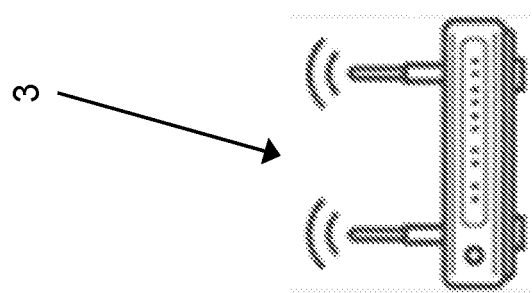
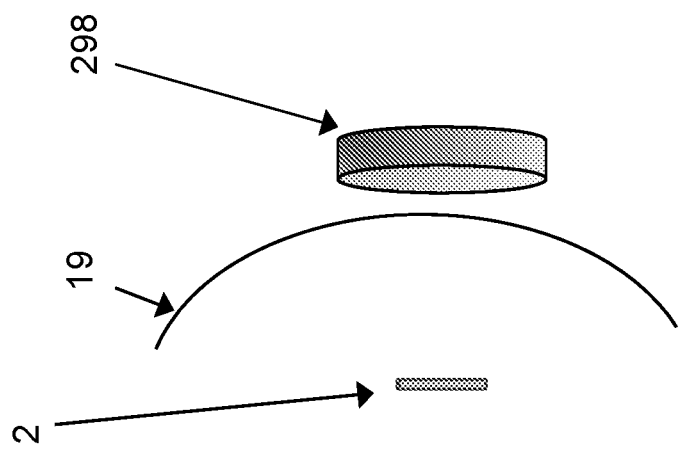
FIG. 2a

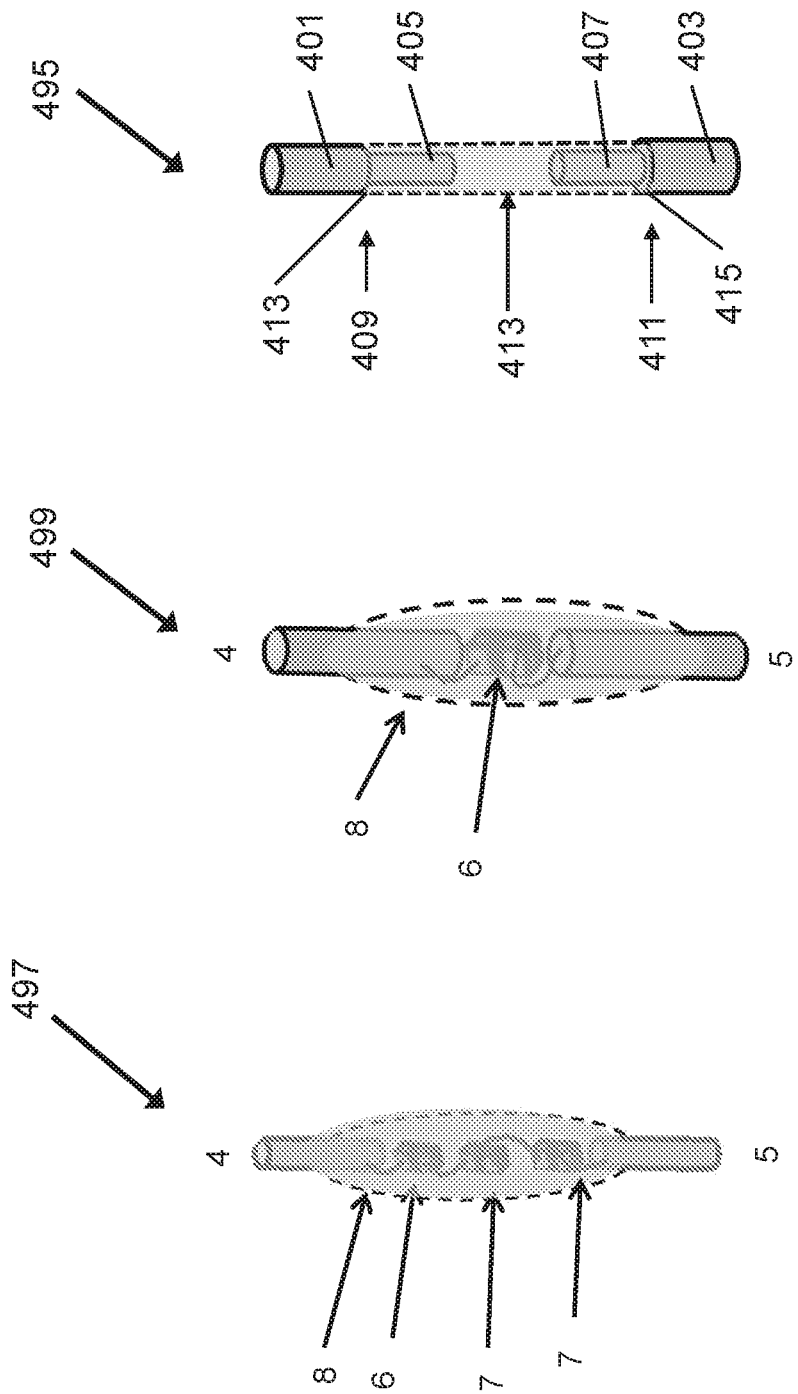

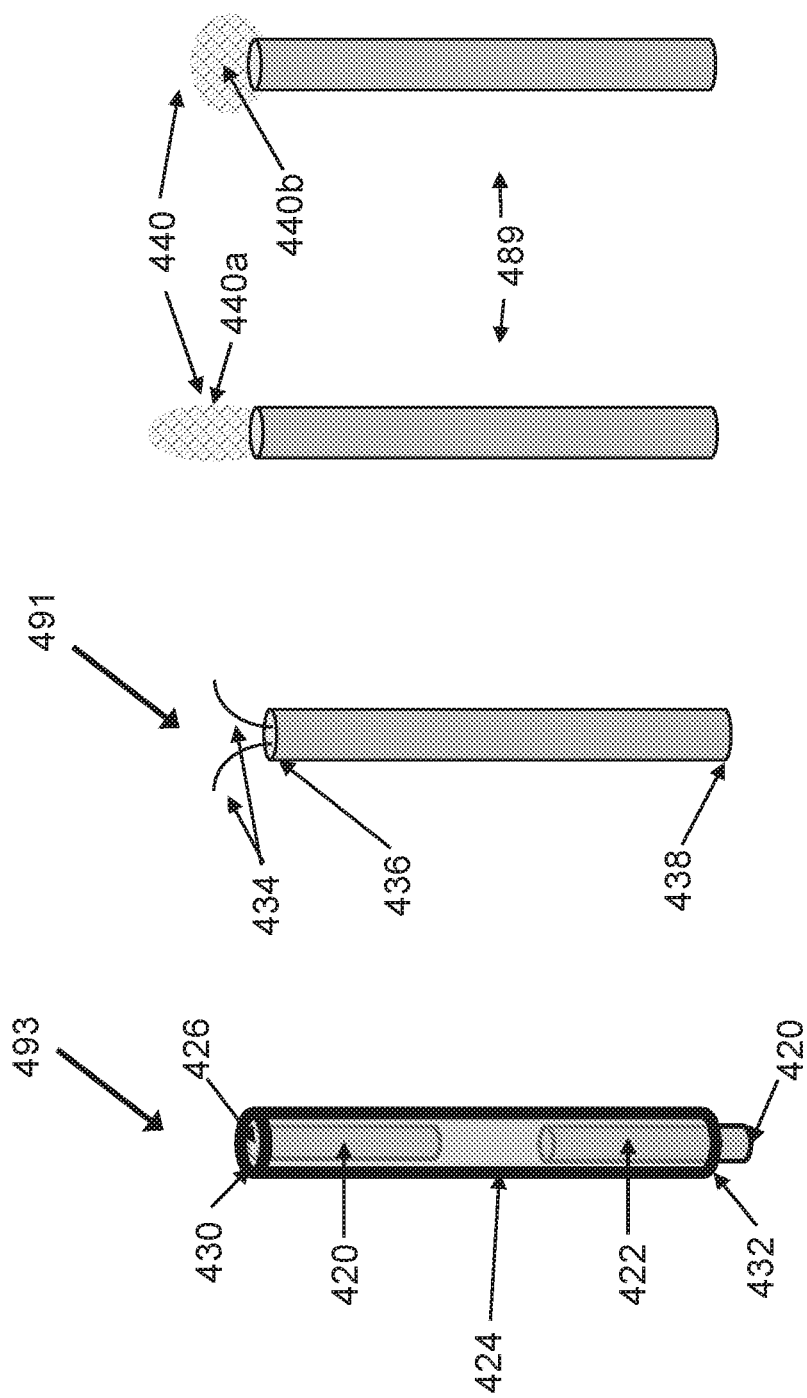

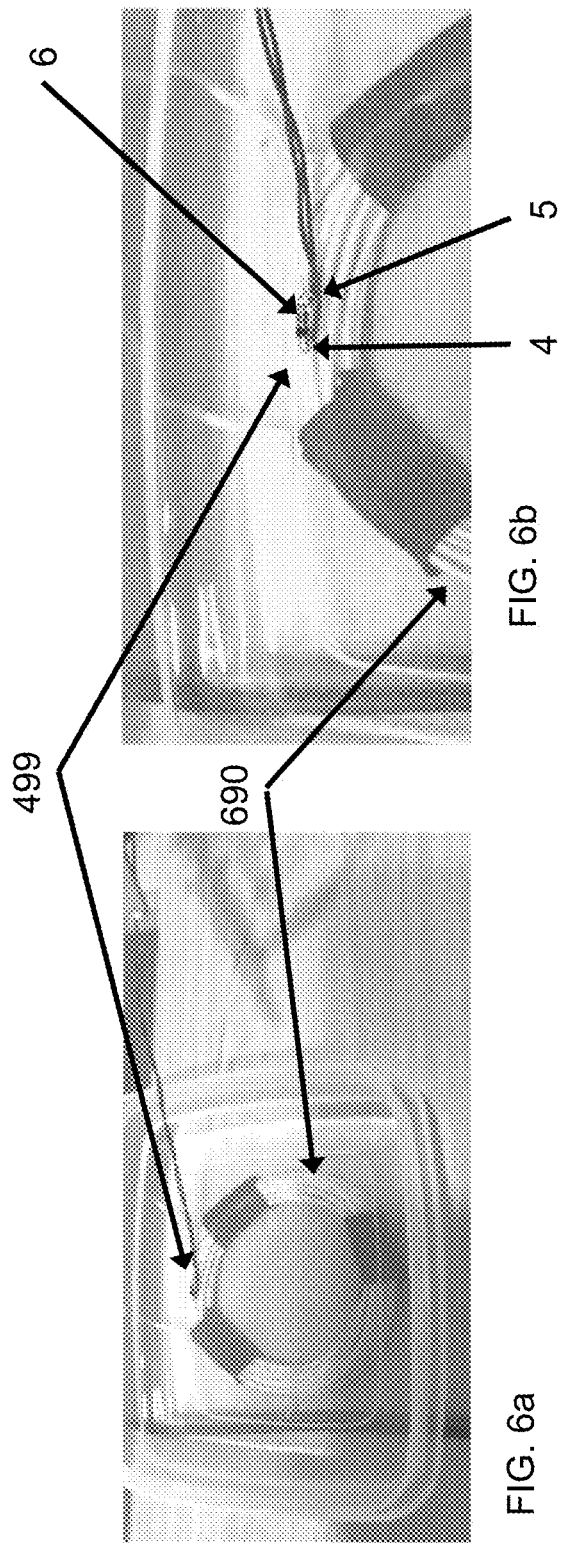
FIG. 6a
FIG. 6b
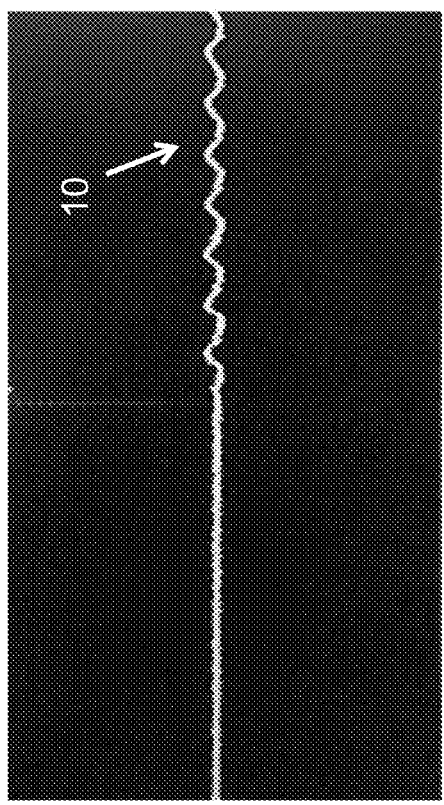
FIG. 6c

| Wearable Design | | | | Injectable Design | | |
|---|---|---|---|---|---|---|
| Coil Turns | 31 | | | Injectable Diameter | 2 | mm |
| Coil Inner Diameter | 4.5 | cm | | Injectable Length | 4 | mm |
| Coil Outer Diameter | 6.5 | cm | | Diode Part Number | ST TMMBAT41 | |
| Coil Resistance | 10 | milliohms | | Diode Type | Schottky | |
| Coil Wire Gauge | 18 | AWG | | Diode Forward Voltage | 0.4 | Volts |
| MOSFET Part Number | Rohm SCT3030KL | | | Electrodes Material | Tin | |
| MOSFET On Resistance | 30 | milliohms | | Stimulating Electrode Diameter | 1.6 | mm |
| MOSFET Rated Voltage | 1200 | Volts | | Stimulating Electrode Length | 0.45 | mm |
| Capacitor Part Number | Kemet PHE450XB4470JB14R17 | | | Return Electrode Width/Height | 1.6 | mm |
| Capacitor Capacitance | 0.047 | Microfarads | | Return Electrode Length | 0.45 | mm |
| Capacitor Rated Voltage | 2000 | Volts | | Insulating Material | Glass | |
| Rectifier Part Number | Vishay S2M-E3/52T | | | | | |
| Rectifier Voltage Drop | 1.15 | Volts | | | | |
| Rectifier Rated Voltage | 1000 | Volts | | | | |
| | | | | | | |
| Wearable Operation | | | | Injectable Operation | | |
| Power Supply Voltage | 17 | Volts | | Distance to Coil | 1 | cm |
| Power Supply Current | 0.1 | Amps | | Burst Frequency | 32 | Hz |
| Power Consumed | 1.7 | Watts | | Burst Duration | 240 | Microseconds |
| Coil-On Duration | 0.261 | milliseconds | | Peak Voltage | 1 | Volts |
| Resonant Peak Voltage | 750 | Volts | | Pulse Width | 6 | Microseconds |
| Resonant Frequency | 83 | KHz | | Electrical Load | Saline 0.9% NaCl | |

FIG. 6d

| Wearable Design | | | Injectable Design | | |
|---|---|---|---|---|---|
| Coil Turns | 31 | | Injectable Diameter | 3 | mm |
| Coil Inner Diameter | 4.5 | cm | Injectable Length | 8 | mm |
| Coil Outer Diameter | 6.5 | cm | Inductor Part Number | Taiyo Yuden CBC3225T101MR | |
| Coil Resistance | 10 | milliohms | Inductor Windings Diameter | 2 | mm |
| Coil Wire Gauge | 18 | AWG | Number of Inductors | 1 | |
| MOSFET Part Number | Rohm SCT3030KL | | Inductor Inductance | 0.1 | millihenries |
| MOSFET On Resistance | 30 | milliohms | Diode Part Number | ST TMMBAT41 | |
| MOSFET Rated Voltage | 1200 | Volts | Diode Type | Schottky | |
| Capacitor Part Number | Kemet PHE450XB4470JB14R17 | | Diode Forward Voltage | 0.4 | Volts |
| Capacitor Capacitance | 0.047 | Microfarads | Electrodes Material | Tin | |
| Capacitor Rated Voltage | 2000 | Volts | Stimulating Electrode Diameter | 1.6 | mm |
| Rectifier Part Number | Vishay S2M-E3/52T | | Stimulating Electrode Length | 0.45 | mm |
| Rectifier Voltage Drop | 1.15 | Volts | Return Electrode Width/Height | 2 | mm |
| Rectifier Rated Voltage | 1000 | Volts | Return Electrode Length | 0.6 | mm |
| | | | Insulating Material | Polyolefin | |
| Wearable Operation | | | Injectable Operation | | |
| Power Supply Voltage | 17 | Volts | Distance to Coil | 1 | cm |
| Power Supply Current | 0.1 | Amps | Burst Frequency | 32 | Hz |
| Power Consumed | 1.7 | Watts | Burst Duration | 240 | Microseconds |
| Coil-On Duration | 0.281 | milliseconds | Peak Voltage | 10 | Volts |
| Resonant Peak Voltage | 750 | Volts | Pulse Width | 6 | Microseconds |
| Resonant Frequency | 93 | kHz | Electrical Load | Saline 0.9% NaCl | |

FIG. 7d

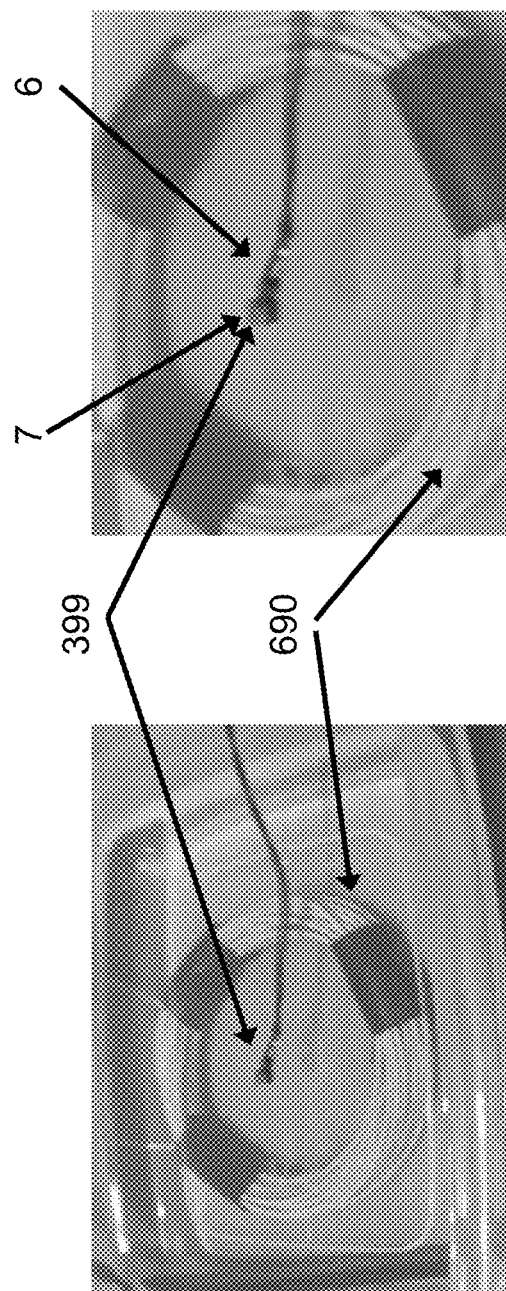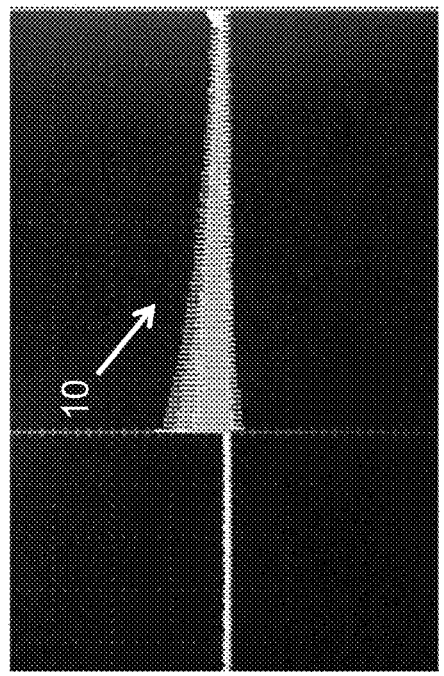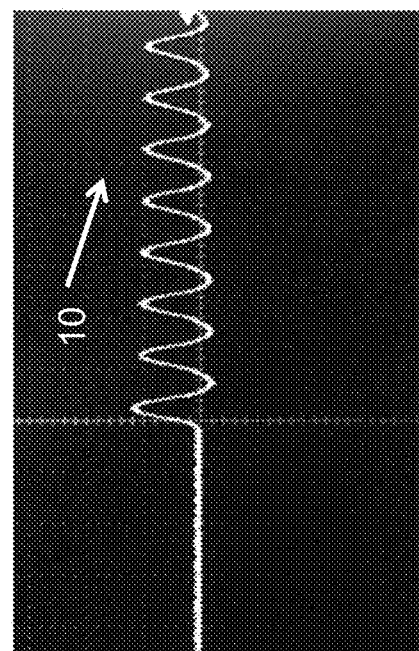
FIG. 8b
FIG. 8d
FIG. 8a
FIG. 8c

| Wearable Design | | | Injectable Design | | |
|---|---|---|---|---|---|
| Coil Turns | 31 | | Injectable Diameter | 3 | mm |
| Coil Inner Diameter | 4.5 | cm | Injectable Length | 8 | mm |
| Coil Outer Diameter | 6.5 | cm | Inductor Part Number | Taiyo Yuden CBC3225T101MR | |
| Coil Resistance | 10 | milliohms | Inductor Windings Diameter | 2 | mm |
| Coil Wire Gauge | 18 | AWG | Number of Inductors | 1 | |
| MOSFET Part Number | Rohm SCT3030KL | | Inductor Inductance | 0.1 | millihenries |
| MOSFET On Resistance | 30 | milliohms | Diode Part Number | ST TMMBAT41 | |
| MOSFET Rated Voltage | 1200 | Volts | Diode Type | Schottky | |
| Capacitor Part Number | Kemet PHE450XB4470B14R17 | | Diode Forward Voltage | 0.4 | Volts |
| Capacitor Capacitance | 0.047 | Microfarads | Electrodes Material | Tin | |
| Capacitor Rated Voltage | 2000 | Volts | Stimulating Electrode Diameter | 1.6 | mm |
| Rectifier Part Number | Vishay 52M-E3/52T | | Stimulating Electrode Length | 0.45 | mm |
| Rectifier Voltage Drop | 1.15 | Volts | Return Electrode Width/Height | 2 | mm |
| Rectifier Rated Voltage | 1000 | Volts | Return Electrode Length | 0.6 | mm |
| | | | Insulating Material | Polyolefin | |
| Wearable Operation | | | Injectable Operation | | |
| Power Supply Voltage | 17 | Volts | Distance to Coil | 1 | cm |
| Power Supply Current | 0.1 | Amps | Burst Frequency | 32 | Hz |
| Power Consumed | 1.7 | Watts | Burst Duration | 240 | Microseconds |
| Coil-On Duration | 0.281 | milliseconds | Peak Voltage | 10 | Volts |
| Resonant Peak Voltage | 750 | Volts | Pulse Width | 6 | Microseconds |
| Resonant Frequency | 83 | kHz | Electrical Load | Saline 0.9% NaCl | |

FIG. 8e

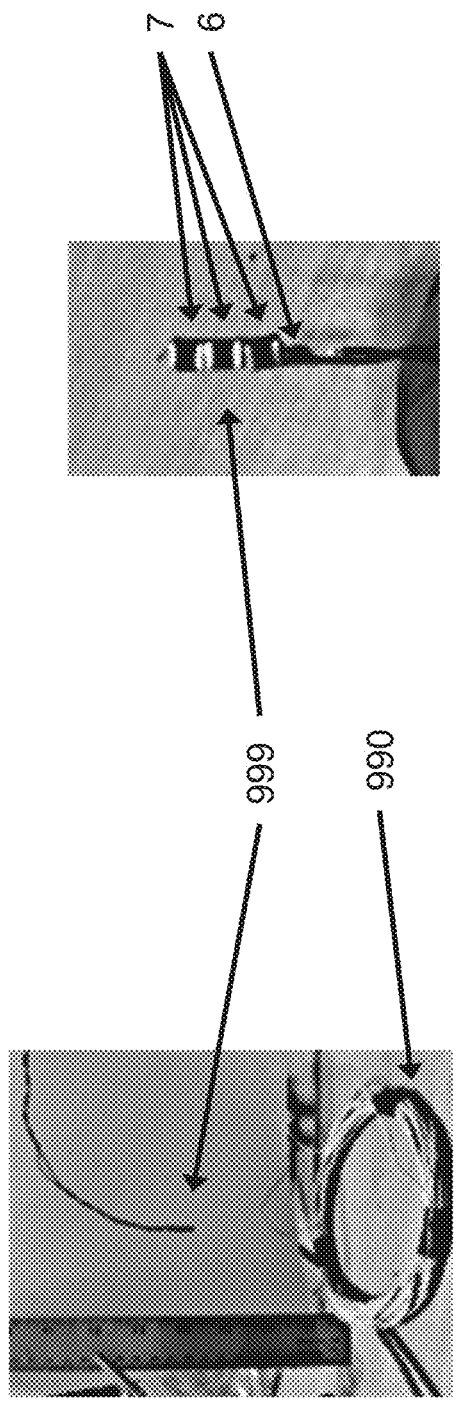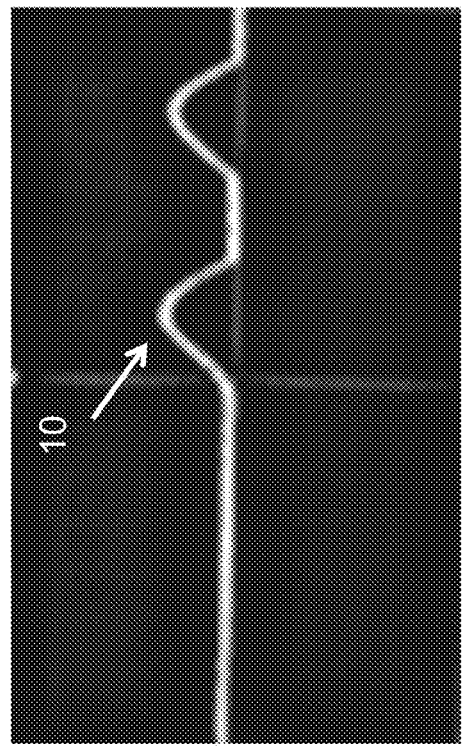
FIG. 9b
FIG. 9a
FIG. 9c

| Wearable Design | | | | Injectable Design | | |
|---|---|---|---|---|---|---|
| Coil Turns | 36 | | | Injectable Diameter | 3 | mm |
| Coil Inner Diameter | 12 | cm | | Injectable Length | 10 | mm |
| Coil Outer Diameter | 14 | cm | | Inductor Part Number | Taiyo Yuden CBC3225T102KR | |
| Coil Resistance | 180 | milliohms | | Inductor Windings Diameter | 2 | mm |
| Coil Wire Gauge | 18 | AWG | | Number of Inductors | 3 | |
| MOSFET Part Number | Rohm SCT3030KL | | | Inductor Inductance | 1 | millihenries |
| MOSFET On Resistance | 30 | milliohms | | Diode Part Number | ST TMMBAT41 | |
| MOSFET Rated Voltage | 1200 | Volts | | Diode Type | Schottky | |
| Capacitors Part Number | Kemet PHE450XB4470JB14R17 | | | Diode Forward Voltage | 0.4 | Volts |
| Capacitors Capacitance | 0.094 | Microfarads | | Electrodes Material | Tin | |
| Capacitor Rated Voltage | 2000 | Volts | | Stimulating Electrode Diameter | 1.6 | mm |
| Rectifier Part Number | Vishay S2M-E3/52T | | | Stimulating Electrode Length | 0.45 | mm |
| Rectifier Voltage Drop | 1.15 | Volts | | Return Electrode Width/Height | 2 | mm |
| Rectifier Rated Voltage | 1000 | Volts | | Return Electrode Length | 0.6 | mm |
| | | | | Insulating Material | Polyolefin | |
| Wearable Operation | | | | Injectable Operation | | |
| Power Supply Voltage | 23 | Volts | | Distance to Coil | 10 | cm |
| Power Supply Current | 0.07 | Amps | | Burst Frequency | 32 | Hz |
| Power Consumed | 1.6 | Watts | | Burst Duration | 600 | Microseconds |
| Coil On Duration | 0.281 | milliseconds | | Peak Voltage | 10 | Volts |
| Resonant Peak Voltage | 800 | Volts | | Peak Current | 10 | Milliamps |
| Resonant Frequency | 31 | KHz | | Pulse Width | 16 | Microseconds |
| | | | | Electrical Load | Saline 0.9% NaCl | |

FIG. 9d

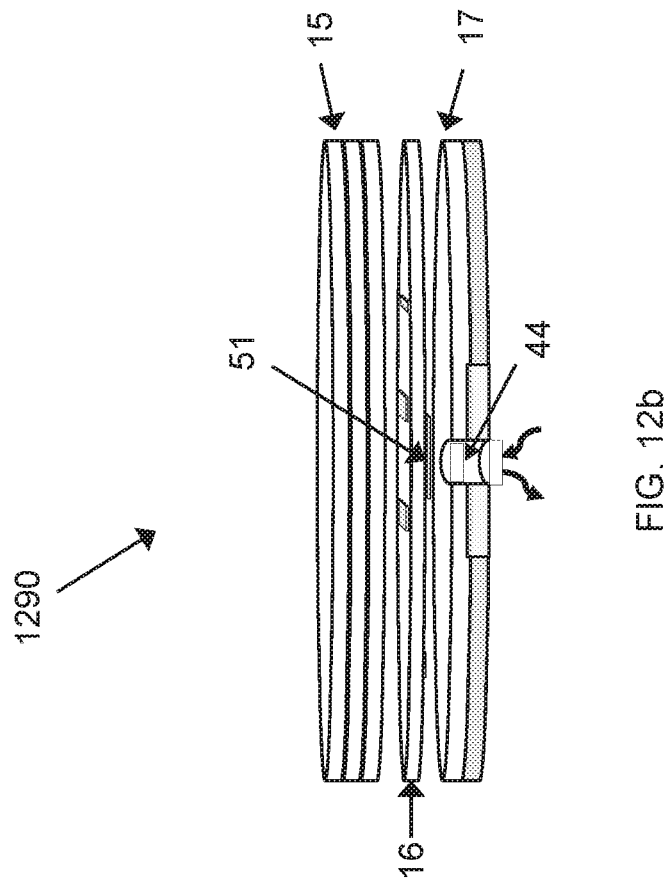
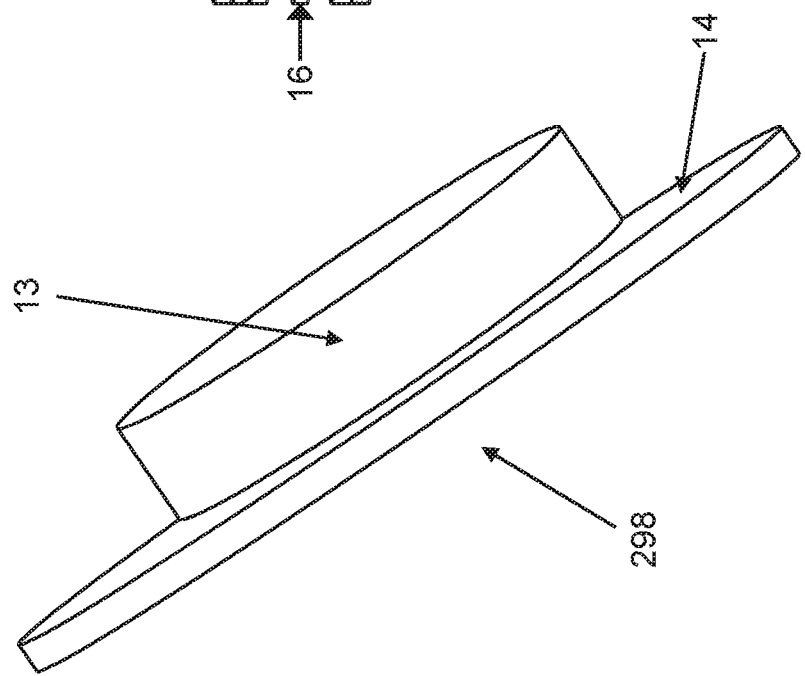
FIG. 12b
FIG. 12a

| Wearable Design | | | | Injectable Design | | |
|---|---|---|---|---|---|---|
| Coil Part Number | TDK WT202012-15F2-ID | | | Injectable Diameter | 3 | mm |
| Coil Turns | 16 | | | Injectable Length | 8 | mm |
| Coil Inner Diameter | 1 | cm | | Inductor Part Number | Taiyo Yuden CBC3225T102KR | |
| Coil Outer Diameter | 2 | cm | | Inductor Windings Diameter | 2 | mm |
| Coil Resistance | 95 | milliohms | | Number of Inductors | 1 | |
| MOSFET Part Number | Rohm SCT3030KL | | | Inductor Inductance | 1 | millihenries |
| MOSFET On Resistance | 30 | milliohms | | Diode Part Number | ST TMMBAT41 | |
| MOSFET Rated Voltage | 1200 | Volts | | Diode Type | Schottky | |
| Capacitors Part Number | C5840C104JCGACAUTO | | | Diode Forward Voltage | 0.4 | Volts |
| Capacitors Capacitance x 3 | 0.3 | Microfarads | | Electrodes Material | Tin | |
| Capacitors Rated Voltage | 500 | Volts | | Stimulating Electrode Diameter | 1.6 | mm |
| Rectifier Part Number | Vishay S2M-E3/52T | | | Stimulating Electrode Length | 0.45 | mm |
| Rectifier Voltage Drop | 1.15 | Volts | | Return Electrode Width/Height | 2 | mm |
| Rectifier Rated Voltage | 1000 | Volts | | Return Electrode Length | 0.6 | mm |
| | | | | Insulating Material | Polyolefin | |
| Wearable Operation | | | | Injectable Operation | | |
| Power Supply Voltage | 7.4 | Volts | | Distance to Coil | 1.3 | cm |
| Power Supply Current | 0.007 | Amps | | Burst Frequency | 32 | Hz |
| Power Consumed | 0.0518 | Watts | | Burst Duration | 50 | Microseconds |
| Coil-On Duration | 0.031 | milliseconds | | Peak Voltage | 12 | Volts |
| Resonant Peak Voltage | 80 | Volts | | Pulse Width | 5 | Microseconds |
| Resonant Frequency | 100 | kHz | | Electrical Load | Saline 0.9% NaCl | |

FIG. 13

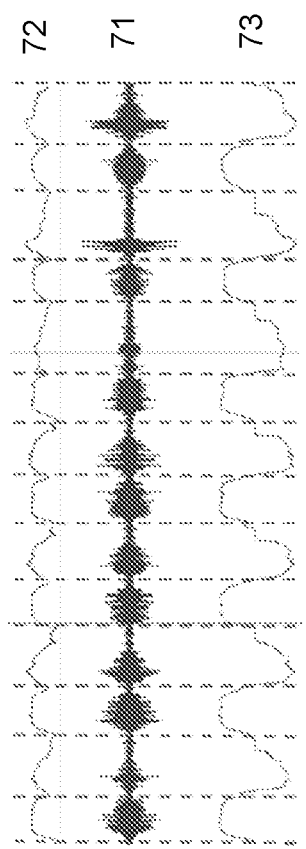
FIG. 15a
FIG. 15b

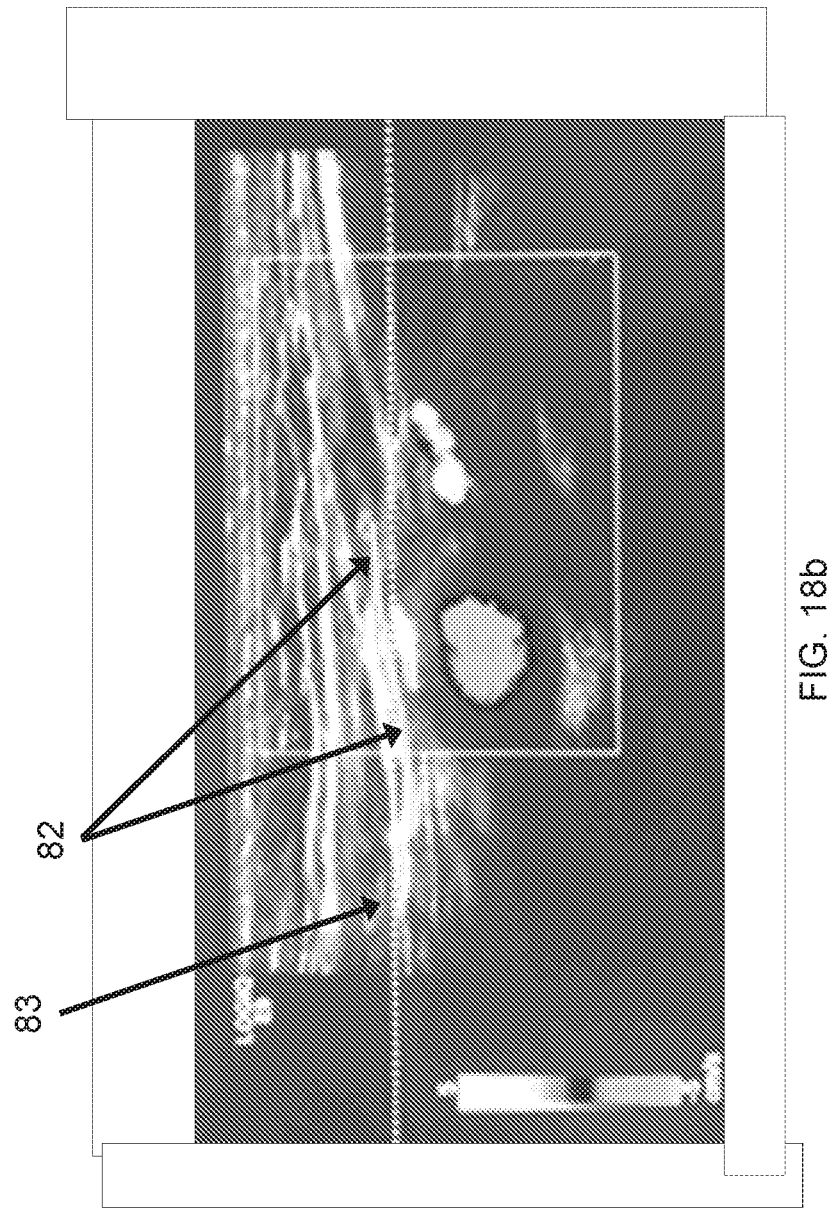
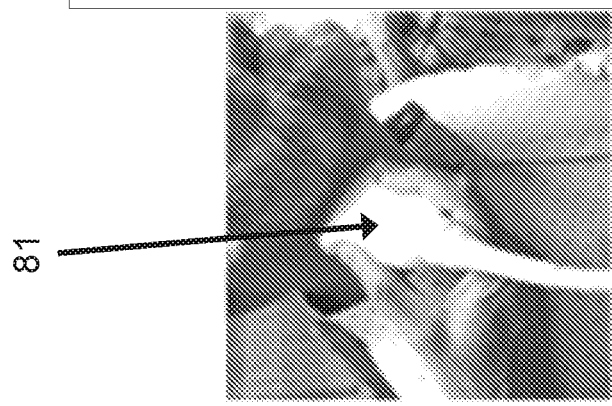
FIG. 18a
FIG. 18b

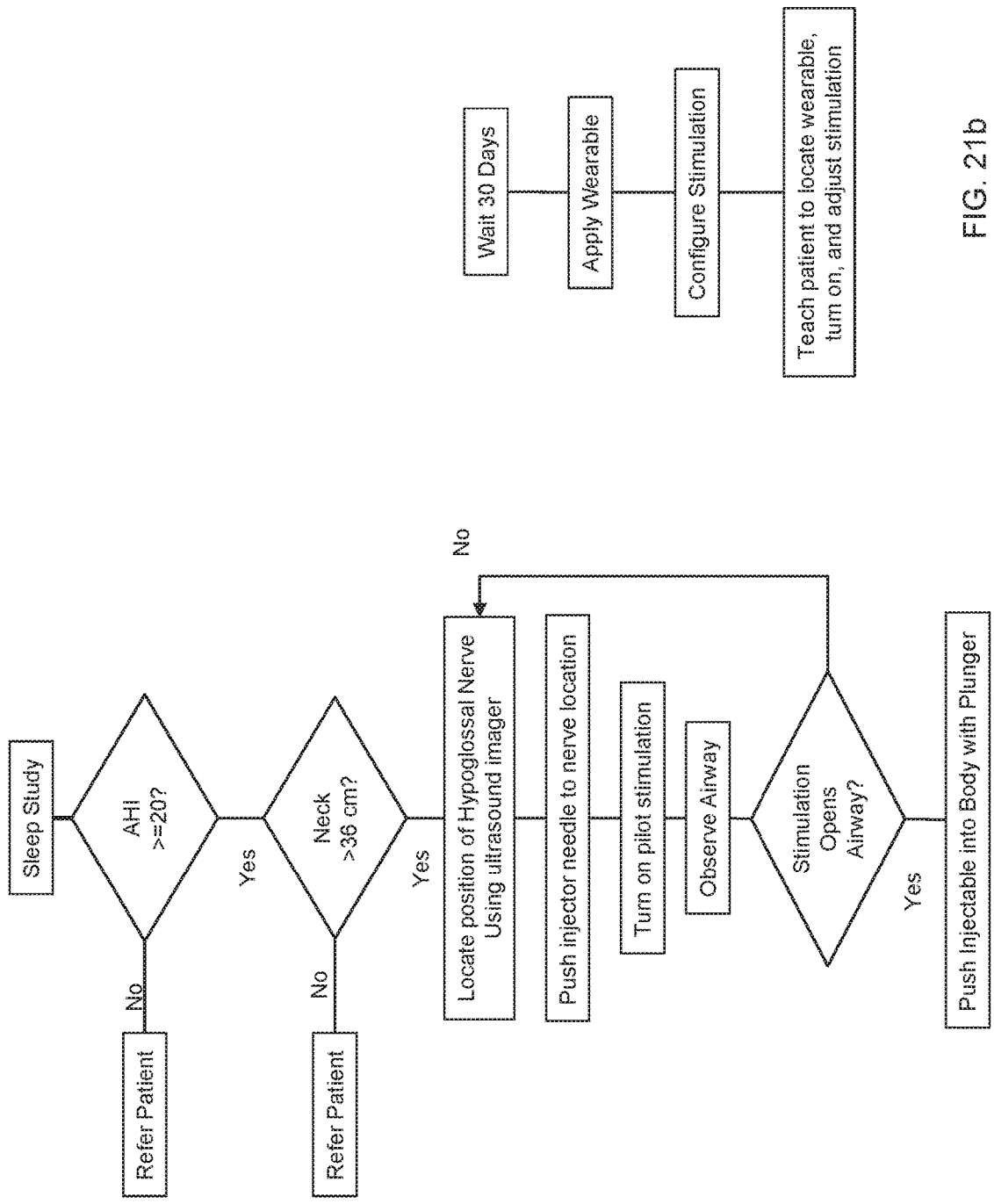

WIRELESS NEURAL STIMULATOR WITH INJECTABLE

CROSS-REFERENCE TO RELATED APPLICATIONS

This application is a U.S. National Stage Application of PCT Application No. PCT/US2019/013538 filed Jan. 14, 2019, which claims the benefit of priority to U.S. Provisional Patent Application Ser. No. 62/617,241, filed on Jan. 14, 2018, U.S. Provisional Patent Application Ser. No. 62/685,860, filed on Jun. 15, 2018, U.S. Provisional Patent Application Ser. No. 62/716,656, filed on Aug. 9, 2018, and U.S. Provisional Patent Application Ser. No. 62/750,326, filed on Oct. 25, 2018 each of which is hereby incorporated by reference in its entirety.

BACKGROUND

The human and mammal bodies use electrical signals to achieve sensory input, muscle movements, thoughts, and memory. Over time, these signals are also responsible for neural plasticity, which includes general wiring, rewiring, and de-wiring of the brain. The electrical signals are represented in the mind and body as potentials (voltages) created by ions, not electrons. However, these ion-transported signals can be initiated, negated, or altered by electric fields that originate from inside or outside the body. By Faraday's law of electromagnetics, these electric fields can be generated from changing magnetic fields, hence, the name "magnetic stimulation". Because these signals are initiated from outside the body, magnetic stimulation can be a non-invasive means for altering or improving of almost all bodily and mental functions.

The signals inside the body are "action potentials" that are pulse-frequency modulated, meaning that the pulse rate is related to the intensity of the sensed input, muscular energy, or neuronal message. The shapes of individual pulses are largely the same throughout, having a pulse width of about 1 millisecond and some undershoot after the main pulse. The pulse height is approximately 70 millivolts for sensory signals and somewhat larger for muscle activation. Pulses for the heart, digestive system, and may other organs have other unique characteristics. For the most part, the signals all look the similar when viewed on an oscilloscope: a "pulse train" wherein the pulse repetition frequency is indicative of the magnitude of the transmitted signal. The absence of a pulse train can also cause a reaction, explaining why amputees still feel parts of the body that no longer exist.

The meaning of the individual signal to the body's nervous system is dependent on where pulse train appears. The brain consists of regions that handle various neural functions and provide input for thoughtful and sensory processing. The peripheral nervous system contains axons that serve as communication channels and repeaters between the sensory nerve endings and the spinal cord and ultimately the brain. The neuromuscular system also consists of axons that communicate in the opposite direction allowing the brain to cause various muscle motions. Axons are grouped together into multi-channel peripheral nerves as they approach the spinal cord or the brain. Some axons are myelinated to increase the propagation rate of the pulse trains to and from the extremities of the body.

Neural stimulation devices strive to create, negate, or alter these naturally-occurring pulse trains in a targeted location to achieve a beneficial result. This may include blocking or stimulation of neural activity. Ultimately, an electric field is required at the location that causes ions to appropriately to trigger an action potential that then can propagate unassisted through the nervous system to its destination. This electric field may be induced rather than generated directly. For example, traditional magnetic stimulation first creates a time-varying magnetic field from a coil of wire, which in turn generates an electric field per Faraday's law. When this electric field is induced on a portion of the neurosensory system, or the neuromuscular system, or brain's neural network, it can alter that system by depolarizing or hyperpolarizing the pulse trains that naturally exist or by inserting a pulse train that does not exist. In the nervous system and the brain, these pulse trains run continuously; only the frequency changes to convey the intensity information.

The prior-art neural stimulation devices fall into three categories: (1) magnetic stimulation wherein changing magnetic fields produced by a coil outside the body generate electric fields inside the body that alters the natural nerve or neuronal signals, (2) skin-electrode stimulation wherein electrodes are placed on the skin and cause current to flow into the body from one electrode to the other, and (3) implanted wire stimulation wherein electrodes implanted at a targeted location and connected by wires to a driver circuit possibly also implanted in another part of the body. Deep Brain Stimulation (DBS) is an example of implanted wire stimulation. Transcranial Magnetic Stimulation (TMS) is an example of magnetic stimulation. Transcutaneous Electrical Neural Stimulation (TENS) and Electro Convulsive Therapy (ECT) are examples of skin-electrode stimulation.

Magnetic stimulation is non-invasive, but unpredictable and low inefficacy because the stimulation is not targeted and the mechanism of action is not understood. Regarding medical treatment, magnetic stimulation has achieved regulatory approval for treating major depression, neuropathic pain, and headaches. According to clinicaltrials.gov, 1165 clinical studies have been or are being performed with "magnetic stimulation" by 427 unique sponsors to understand its effect on 450 different conditions. Magnetic stimulation may include a single external coil, multiple external coils for better targeting such as US 2012/0302821 A1 and also wearable coils such as U.S. Pat. No. 9,072,891 B1 and US 2010/0160712 A1.

Skin-electrode stimulation is non-invasive, but untargeted and uncontrollable because the electrical current follows multiple paths with varying intensity. The mechanism of action of skin-electrode stimulation is not understood except for ECT where an electrical jolt is large enough to intentionally produce a full seizure in the brain. ECT and TENS are approved for very few indications and efficacy is low.

Implanted wire stimulation is highly targeted, but also highly invasive and unstable due to electrode movement from wire-tugging during bodily motions. Infection is also a disadvantage especially if the driver circuit is not implanted.

SUMMARY

The embodiments described herein addresses certain limitations of prior-art magnetic stimulation, skin-electrode stimulation, and implanted wire stimulation. Hence, these embodiments are expected to greatly advance the state of the art for the benefit of mankind.

In one or more embodiments, a wireless neuromodulation system is provided to allow wireless stimulation to eliminate surgery and reduce the complexity to one injection at each desired location of stimulation, and/or make the injectable piece so small that it will not move around overtime in an active human body. These objectives are achieved with this embodiment.

The neural stimulator embodiments described herein may use an external coil to produce changing magnetic fields outside the body, in conjunction with one or more tiny injectable objects that concentrates the field to a highly-targeted location. These systems also add a driver circuit for the magnetic coil that allows for high voltage and fast pulses in the coil, while requiring low-voltage power supply that could be a wearable battery. The coil and driver circuit and battery are also small enough to be easily wearable.

Miniaturization of the magnetic field generator may be achieved using (1) an efficient driver circuit that enables hundreds or thousands of volts in the coil from a low voltage battery, (2) an injectable field concentrator that targets the stimulation to an area as small as microns if desired, and/or (3) a fast rise time in the current of the coil that induces a large electric field to evoke an action potential.

Some of the systems disclosed herein use an electronic circuit to drive the stimulator coil or coils by stimulating a pulse as multiple decaying cycles of a resonance of the stimulator coil combined with a capacitor. Once the decay of the resonance is complete, the circuit remains turned off until the desired time for the next pulse.

By using this approach, the inductive energy of the stimulating coil is recycled through the capacitor, and therefore not wasted on each cycle. In addition, the voltage across the capacitor can reach hundreds or thousands of volts even when the supply voltage is very low. This high voltage internal to the capacitor is then used to rapidly change the current in the stimulating coil for the next pulse. The recycling of the inductive energy also allows for the stimulating coil to have more turns, and therefore needs less current flow to create the same magnetic field strength. The preferred embodiment can create the needed magnetic field pulses with power supply in the range of 3 to 45 volts DC and an average current flow from the supply of 0.1 to 3.0 amps.

In some embodiments of the systems, in addition to providing a smaller injectable, the healthcare provider or the user/wearer still has the flexibility to set the signal parameters as needed for effective neural stimulation. These include (1) set the amplitude of the stimulating pulses by adjusting the supply voltage or by adjusting the turn-on time of the circuit, (2) set individual pulse width by selecting the appropriate capacitor, (3) set the burst frequency by using a programmable digital pulse generator, (4) achieve a desired penetration depth by sizing the diameter of the coil, and/or (5) set the duration of the stimulation session by turning the whole system on and off. Hence, many key parameters are easily tuned to implement or derive the clinical or therapeutic protocol for neural stimulation. The electronic components mentioned above may be controlled by a microprocessor or computer to achieve pre-programmed stimulation protocols.

In one embodiment, a neuromodulation system may be provided, comprising at least one elongate injectable configured for placement inside the body with one end adjacent to the site to be stimulated, and a magnetic field generator configured to be placed outside the body and to generate a time varying magnetic field with a specified orientation relative to axes of a diode, and possibly an inductor, component in the injectable. The tissue-exposed surfaces of the elongate injectable may comprise a material selected from a group consisting of a metal for the electrodes and an insulator encapsulation. The metal surface may be copper, tungsten, chromium, steel, stainless steel, nickel, nichrome, titanium, gold, silver, brass, platinum, iridium, platinum-iridium or any alloy thereof. The insulator surface may comprise PTFE, nylon, silicone, polyethylene, polyurethane, latex, polyimide, BoPET, or any combination thereof. The elongate injectable may be configured for placement adjacent of an electrode to a peripheral nerve, spinal nerve, brain-stem nerve, or brain neuron or other neuron or axon. The elongate injectable may comprises a cylindrical shape with a diameter and a length, wherein the diameter may be less than the length. The elongate conductor may be a structure with no curves or angled bends along its longitudinal axis. The elongate conductor may comprise a diode or a diode with an inductor or multiple inductors, for example. The elongate conductor may be injected into the body through a guiding tube, such as a needle of a syringe or other introducing device. The magnetic field generator may comprise a coil, the coil comprising one or more coil windings of wire, possibly stranded wire wherein the strands are insulated from one another. The magnetic field generator may be connected in parallel with a capacitor and configured such that a stimulation signal may generated, result from, or defined by a portion in time of a resonance between the coil and the capacitor. The parallel capacitor and coil may be configured to be activated by a DC power supply or battery on one side and a switch to ground on the other side, wherein a time period between the switch closing and the switch opening builds up the electrical current in the coil, and the time after switch opening presents the decaying resonance that induces a burst of stimulation pulses. The switch may be a combination of a transistor and a rectifier and a switching action may be configured to occur by turning the transistor on or off by applying a voltage to a gate or a base of the transistor. The magnetic field generator may comprise a stimulator coil, the stimulator coil comprising a material with high magnetic permeability configured to contain the fringe fields. The material with high magnetic permeability may comprise rigid or flexible ferrite, steel, or iron. The coil may further comprise a conducting ferromagnetic material that reduces the amplitude of subsequent resonant pulses relative to the prior pulses. The material may comprise iron, cobalt, nickel, steel, or an alloy or other combination thereof. The one or more coil windings may be in a plane or multiple adjacent planes, The one or more coil windings may comprise magnet wire or bundled strands of magnet wire, each strand insulated or not. The one or more coil windings may comprise metal deposited on a layered substrate. The substrate may be rigid, and may optionally comprise FR-4 glass-reinforced epoxy laminate, glass, or hard plastic. In other embodiments, the substrate may be flexible. The flexible substrate may comprise polyimide, BoPET, polyethylene, polyurethane, nylon, or PTFE. The system may further comprise one or more of a microprocessor, rechargeable battery, disposable battery, user interface, physician interface, nurse interface, data storage, and network connection. The network interface may be configured to monitor or control the stimulator by a computer or base station, by the user, or by a professional or to gather data or statistics therefrom. The elongate injectable may comprise passive electronic components, and may lack a battery, may lack feedback circuitry, may lack voltage conversion circuitry, and/or may lack power management circuitry.

In another embodiment, a method of treating a condition is provided, comprising identifying a patient with one or more elongate injectables, placing a coil of an external magnetic field generator against a surface of a treatment site of the patient, and applying a magnetic field to the one or more implanted elongate conductors to generate therapeutic neural stimulation. The method may further comprise activating the magnetic field generated to, modulate, increase or decrease action potential activity at the treatment site. The action potential activity may be located in neurons in the brain, sensory system, or neuromuscular system. The method may be used in the treatment of a pain disorder, mental disorder, sensory disorder, or muscular disorder, and the pain disorder may be due to amputation, neuropathy, nerve damage, or injury. The mental disorder may be depression, Huntington's disease, Alzheimer's disease, dementia, anxiety, insomnia, post-traumatic stress disorder, and/or panic attacks. The muscular disorder may be sleep apnea, bladder incontinence, fecal incontinence, sexual dysfunction, tremor, or ticks. The method may further comprise generating the magnetic field using less than 100 peak amps and 100 volts of peak voltage.

In still another embodiment, a treatment device is provided to introduce the injectable into the body, comprising a syringe or injector body, a sliding plunger or pushrod located in the syringe or injector body, a needle attached to the syringe or injector body, and at least one discrete elongate injectable located in the syringe or injector body, wherein the syringe or injector body and needle restrain the orientation of the at least one elongate injectable, and wherein the elongate injectable comprises a number of passive electronic components.

In another embodiment, a neuromodulation system is provided, comprising at least one elongate injectable with a length of less than ten millimeters and a transverse dimension to the length of less than three millimeters, configured for implantation adjacent or against a nerve, axon, or neuron, and a magnetic field generator that may be spaced apart from the at least one elongate injectable, and configured to generate an induced voltage between a pair of electrodes of at least one elongate injectable. The at least one elongate injectable may be pre-loaded in an injection device and in a sealed sterile package. The magnetic field generator may further comprise a rechargeable battery or a disposable non-rechargeable battery. The magnetic field generator may be located in a housing comprising at least one of an adjustable strap, elastic band, hook-and-loop connector, buckle, adhesive, or pin, that is configured to attach the housing a location on a human body or in attire or pockets thereof worn by the human body. The housing may have a height relative to a skin surface at the location on the human body that may be less than two centimeters.

In another embodiment, a method of treating a patient is provided, comprising inserting at least one elongate injectable against or adjacent to a nerve, axon, neuron or neural tissue, wherein the injectable has a length of less than ten millimeters and a transverse dimension to the length of less than three millimeters, positioning a magnetic field generator at a location spaced away from the at least one elongate injectable, and using the magnetic field generator to provide an induced voltage between a pair of electrodes on at least one elongate injectable. The magnetic field generator may be an ambulatory magnetic field generator comprising a housing with a plurality of magnetic coils, a driver circuit, and a rechargeable or disposable battery. The plurality of magnetic coils has a net thickness of less than three centimeters. The at least one elongate injectable may be against a skin surface. The method may further comprise maintaining the location of the magnetic field conductor using at least one strap, elastic band, hook-and-loop connector, buckle, adhesive, pin, or pocket.

In another embodiment, the field generator also contains sensors, including an oxygen saturation level sensor, a plethysmograph sensor, a vibration sensor, or a microphone. The oxygen saturation sensor or the plethysmograph sensor may contain pairs of light-emitting diodes and photosensors that sense redness of the tissues or expansion and contraction of the tissues in response to breathing and heart beats, or both of these. These sensors may have their outputs processed, using analog or digital signal processing, or both, possibly including Fourier or other linear transformations, filtering, peak detectors, amplitude detectors, polarity detectors, or envelope detectors, to monitor body and health parameters like breathing rate, breathing duty cycle, distinguishing inhaling from exhaling, snoring, partial breathing obstructions or hypopneas, full breathing obstructions or apneas, heart rate, blood pressure, breathing effectiveness, and blood oxygen levels. Information processed from these sensors may be used to determine stimulation turn-on and turn-off times, the amplitude of the stimulation, the specific or general health of the user, the effectiveness of the stimulation, or be gathered as useful general information for later processing. This information may be communicated from the field generator to a secure database, directly or through an intermediate base station.

BRIEF DESCRIPTION OF THE DRAWINGS

FIG. 2a is a schematic representation of exemplary components of the neural stimulation; FIG. 2b depicts an embodiment of the needle syringe delivery device with the injectable;

FIG. 4a is a graphical representation of the elongate injectable with a second inductor to increase the amplitude of its output. FIG. 4b is a graphical representation of the elongate injectable with a diode only for stimulation applications requiring a lower amplitude and a smaller injectable. FIG. 4c is a graphical representation of the elongate injectable with a different encapsulation profile. FIG. 4d is a graphical representation of the elongate injectable with yet another encapsulation profile. FIG. 4e is a graphical representation of the elongate injectable with strands emanating from one end. FIG. 4f is a graphical representation of the elongate injectable with a mesh emanating from one end prior to injection. FIG. 4g is a graphical representation of the elongate injectable with mesh expanding after placement in the body;

FIG. 6a shows the apparatus to test the output amplitude of the elongate injectable containing one diode and no other electronic components, and placed in a saline bath that simulates human tissue for an embodiment wherein the diode is oriented along and spaced above the windings of the wearable coil;

FIG. 6b is a magnified version of FIG. 6a;

FIG. 6c shows the oscilloscope trace of the output of the elongate injectable for the embodiment of FIG. 6a and FIG. 6b;

FIG. 6d shows the details and test results of an embodiment shown in FIG. 6a;

FIG. 7b shows an oscilloscope trace of the output of the elongate injectable for the embodiment of FIG. 7a;

FIG. 7d shows the details and test results of an embodiment shown in FIG. 7a;

FIG. 8a shows the apparatus to test the output amplitude of the injectable placed in a saline bath that simulates human tissue for an embodiment wherein the one inductor of the elongate injectable is now located along and oriented along the center axis of the wearable coil;

FIG. 8b is a magnified version of FIG. 8a;

FIG. 8c shows an oscilloscope trace of the output of the elongate injectable for the embodiment of FIG. 8a and FIG. 8b;

FIG. 8d is the oscilloscope trace of FIG. FIG. 8c with a different time scale;

FIG. 8e shows the details and test results of an embodiment shown in FIG. 8a;

FIG. 9a shows the apparatus to test the output amplitude of the injectable connected to a resistor that simulates the electrical properties of human tissue for an embodiment wherein the elongate injectable contains three inductors and one diode, and all three inductors are serially placed above and all three have their windings oriented along on the center axis of the wearable coil, but now the distance away from the wearable coil center is much larger than in FIG. 8a;

FIG. 9b is a magnified view of the elongate injectable in FIG. 9a.

FIG. 9c is an oscilloscope trace of the output of the injectable of the apparatus of FIG. 9a.

FIG. 9d shows the details and test results of an embodiment shown in FIG. 9a.

FIG. 12a shows the permanent and disposable parts of the wearable of an embodiment.

FIG. 12b shows a hardware configuration of the permanent parts of the embodiment wearable including the coil, the circuit board, the battery, the sensors, and others;

FIG. 12d is a side view of the coil of FIG. 13a.

FIG. 12e is a stack up view of the coil of FIG. 13a.

FIG. 13 shows the details and test results of an embodiment for sleep apnea treatment.

FIG. 15a shows the output signal and the output signal envelope of a microphone when placed near the location of an embodiment of the wearable field generator for treating Obstructive Sleep Apnea.

FIG. 15b shows how the output signal of FIG. 15a changes during breathing obstruction;

FIG. 18a shows the apparatus used to create ultrasound images of the body including the hypoglossal nerve of a human subject.

FIG. 18b shows the resulting images with the location of the hypoglossal nerve highlighted as an edited-in overlay to the image;

FIG. 19b is intended to be an electrically equivalent apparatus to the embodiment treatment for Obstructive Sleep Apnea;

FIG. 20b shows the protruding tongue position of a human subject using the apparatus of FIG. 19b with stimulation turned on;

FIG. 21a shows a portion of a treatment procedure for obstructive sleep apnea using an exemplary embodiment for placing the internal part into the patient.

FIG. 21b shows the remainder of the treatment procedure for applying and configuring the wearable part and training the patient on use.

DETAILED DESCRIPTION

Figure 1:
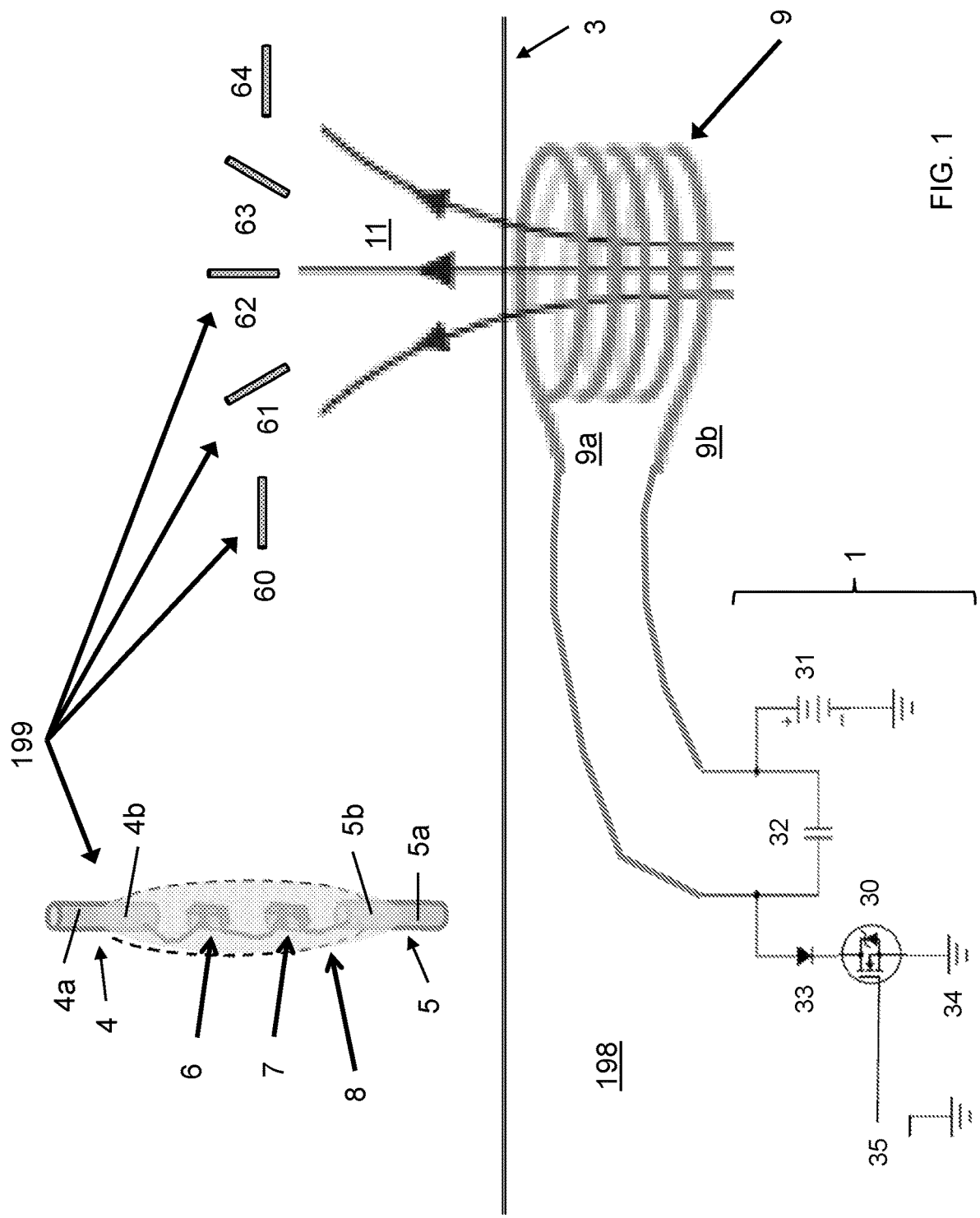
FIG. 1 is a schematic representation of a wearable stimulator coil which is pulse-driven by a driver circuit, combined with an elongate injectable containing a diode and an inductor that concentrate the field produced by the stimulator coil's changing magnetic field.

FIG. 1 is a schematic diagram showing one embodiment of a neuromodulation system. A driver circuit 1 of a wearable field generator 198 produces repeatable bursts of decaying resonance between coil 9 and capacitor 32. The resulting current flow in coil 9 produces a changing magnetic field that penetrates deep in to the body 3, including hard and soft tissue. This changing magnetic field, by Faraday's law of electromagnetics, induces an electric voltage at either end of an elongate injectable conductor 199. A diode 6 is added to rectify the induced voltage for monophasic stimulation. In order to increase the induced voltage at the injectable still further, an inductor 7 is added in series with the diode 6, wherein the axis of the inductor windings is the same as the axis of the rest of the elongate injectable 199. The changing magnetic field from the coil 9 that intercepts the windings of the inductor 7 produces an additional voltage, like a transformer, that adds to the induced voltage. The diode 6 and the inductor 7 are electrically in series between the stimulating electrode 4 and the return electrode 5. Either the inductor 7 or the diode 6 may be connected to the stimulating electrode 4, but in some embodiments, having the inductor closer to the skin will reduce the depth of penetration required of the magnetic field, and correspondingly reduce the power consumption and increases the battery life of the wearable. In some embodiments, the stimulating electrode 4 is in direct electrical connection to the diode 6, e.g. without any intervening electronic components, which in turn is in direct connection to the inductor 7, which is in direction connection to the return electrode 5. In this example, no capacitors or batteries are provided in the injectable conductor 199, and thus the injectable conductor is directly powered or driven by the wearable generator 198 via its coil 9.

The cross-sectional dimension of the stimulator coil 9 in FIG. 1 is typically between 1 and 20 cm, which needs to be small enough to be comfortable as a wearable, but also large enough to have a penetration depth to reach the injectable. Some stimulation sites for the injectable like the Hypoglossal nerve are within 1-2 cm, but other stimulation sites like the spinal cord could be 20 cm deep for an obese patient. The proper location and orientation of the wearable may be marked by one or more tattoos, scars, or other permanent fiducial markings placed on the skin by a medical professional during initial treatment. Subsequently, the patient or companion is able to locate the wearable properly without the supervision of a professional.

The driver circuit 1 of the wearable field generator 198 in FIG. 1 of the neural stimulator system manages the applied voltage, current, and power consumption of the stimulating coil 9 effectively to reduce one, two, or all three of these quantities. The pulse current of the driver circuit 1 changes rapidly in the coil 9, creating a rapidly changing magnetic field 11, thereby creating the large electric field, by Faraday's law, a few centimeters away and inside the body 3. The voltage generated in the wearable capacitor 32 during resonance can be many times greater than the supply voltage required of the circuit 1. Hence, the driver circuit 1 can use high voltages to achieve a rapid change in current in the stimulating coil 9 without requiring a high voltage supply. The ability of this embodiment to generate a more intensely varying magnetic field 11 reduces the size of the implant that resides inside the body 3. By Faraday's law of induction, the necessary cross-sectional area of the implant is proportional to both the magnitude and the rate of change of the magnetic field 11. Hence, a stronger time-varying magnetic field leads to a smaller internal part.

In FIG. 1, a series connection of a rectifier 33 and an N channel MOSFET 30 together act as an analog switch controlled by a pulse generator 35 applied to the gate of MOSFET 30. A MOSFET normally functions as an ideal switch, but only when the drain-source voltage is positive. Because the drain-source voltage can sometimes be negative, as will be described later, the rectifier 33 is added in series to prevent the MOSFET 30 from seeing a negative drain-source voltage and preserving characteristics of an ideal analog switch that is open.

One terminal 9a of coil 9 is connected to a DC power supply or battery 31. Each pulse from the pulse generator 35 in FIG. 1 allows current to build up in coil 9 by connecting the other terminal 9b of coil 9 to ground, completing the circuit. The pulse width can determine how much current is flowing in coil 9 and hence the amplitude of the decaying resonance between coil 9 and capacitor 32 that occurs at the end of the pulse when connection to ground is opened. The decaying resonance defines a stimulation burst. The current that has built up in the coil 9 at the end of the pulse determines the burst amplitude.

Typically in neural stimulation, the burst frequency can be between 10 Hz and 100 Hz, but in other examples could be 1 Hz to 10 Hz or 100 Hz to 1000 Hz, or 1 kHz to 10 kHz. The time period between the bursts in seconds is the inverse of the frequency in Hz, and typically is between 10 milliseconds and 100 milliseconds, or could be 100 milliseconds to 1 second or 1 millisecond to 10 milliseconds. The burst duration is typically 50 to 1000 microseconds long. The amplitude needed at the injectable for neural stimulation are typically 0.01 volts to 20 volts. For example, some stimulation protocols just need to regenerate background levels of neural activity while others need to evoke the maximum rate of action potentials of the body. Stimulating muscle movements, for example, require strong stimulations to recruit most or all the muscle fibers to act together as each one is activated by a single nerve fiber. The ranges of burst amplitude and burst frequency could also be dependent on how close the injectable is placed to the target nerve or nerve fibers or neurons to be stimulated. In some cases, the target nerve group or nerve fiber may be deep within the nerve, and the stimulation from the injectable must traverse one of more fascicles, which shield the stimulation energy, possibly differently for some frequencies versus others. For example, if higher frequencies of stimulation from the injectable are attenuated by the soft tissues in the body, then the wider pulse widths and lower burst frequencies would traverse these tissues with less attenuation than narrower pulse widths and higher burst frequencies. The location of nerve groups within a nerve and nerve fibers within a group are not always the same from one patient to another, and the injectable may need to stay a safe distance away to prevent nerve damage throughout the life the patient. The neural stimulator embodiments described herein can achieve a range of stimulations using the injectable conductor combined with the wearable stimulator.

In FIG. 1, the burst rate of stimulation is set by the frequency of the pulse generator output 35. The elapsed time between the start of stimulation pulses to the termination of pulses, or burst width, is set by the period of decay of the resonance between coil 9 and capacitor 32. Finally, the width of individual stimulation pulses is determined by the resonant frequency of the stimulator coil 9 and the parallel capacitor 32, and this resonant frequency can easily be adjusted by changing the capacitance of the parallel capacitor 32. In many embodiments, the capacitance of the capacitor is between 0.01 microfarads and 1.0 microfarads, but in other embodiments could be between 0.001 and 0.01 microfarads or between 1.0 and 10.0 microfarads. The amplitude of the burst is determined by the how long the logic signal 35 is turned on. Hence, all key parameters of known and desirable wired stimulations systems can be accommodated by the system of FIG. 1. Thus, the stimulation is able to achieve the flexibility needed for individual patients and therapies while providing for a smaller injectable component.

Without limitation, the rectifier 33 in FIG. 1 may each be multiple rectifiers ganged together in series or in parallel or both to distribute the current and voltage and stay below the rated voltage and/or rated current of each individual rectifier. Also, without limitation, the MOSFET 30 of FIG. 1 may each have multiple MOSFETs connected in parallel or series for the same purpose. In addition, these MOSFETs could be replaced by Insulated Gate Bipolar Transistors (IGBTs), Darlington transistors, or bipolar transistors, without limitation. Also, without limitation, the output of the pulse generator may originate from a microprocessor-based controller or computer and have multiple transistor driver stages to adequately turn on and off the MOSFETs or other driver transistors. Again, without limitation, multiple instances of this driver circuit could be used to drive multiple coils synchronously for the fields of the multiple coils to add together in a focused region or subtract to remove stimulation where it is not wanted, or any combination of these. Two coils may be used to better focus the magnetic field inside the body at the injectable.

The injectable 199 in FIG. 1 contains the diode 6 and inductor 7 connected in series between two electrodes 4 and 5. Stimulating electrode 4 is located is close to the nerve, axon, or neurons to be stimulated. Return electrode 5 completes the electrical circuit within the body, and it may be placed in a location that will not cause unintended stimulation. Without limitation, return electrode 5 can have a larger overall surface area than the stimulating electrode 4, as lower current densities are less likely to stimulate. The electrodes 4 and 5 are electrical conductors that are exposed to bodily tissue. Encapsulation material 8 houses the electronic components and insulates the rest of the circuit electrically from the body. The exposed regions of the electrodes 4 and 5 and the encapsulation material 8 are biocompatible as the injectable 199 is intended to reside the body 3 for a long time, possibly for the life of the patient.

The diode 6 in FIG. 1 could be a silicon diode, Schottky diode, or a Zener diode, for example. A silicon diode can have the smallest relative size, but typically has a higher threshold voltage that subtracts, on average, from the stimulation voltage making it less efficient. A Schottky diode has a lower threshold voltage but typically is larger in size. A Zener diode has the same the threshold voltage as a silicon diode but has the added advantage of being able to limit the voltage applied to the body to a safe level.

The inductor 7 in FIG. 1 may include ferrite inside of its windings or completely surrounding its windings to concentrate the magnetic field generated by coil 9. The size of the inductor 7 determines the amount of power that can be delivered to the electrodes, per Faraday's law of electromagnetic induction. As will be shown in the examples, the inductors' diameters can be as small as 2 mm for neural stimulations as deep as 10 cm. This allows the injectable diameter to be as small as 3 mm after encapsulation. An injectable of this diameter reduces the invasiveness to a single injection and eliminates the need for surgery and for general anesthesia.

To provide the reduced profile suitable for injection or minimally invasive implantation, the injectable 199 may comprise an elongate structure with a longitudinal axis, with the stimulating electrode 4, diode 6, inductor 7 and return electrode 5 electrically connected in series and physically located in the recited order along the longitudinal axis. The electrodes 4 and/or 5 may each have an elongate configuration as depicted in FIG. 1, e.g. an oblong or cylindrical body with a longitudinal axis that may or may not be axially aligned with the longitudinal axis of the overall injectable 199. The electrodes 4 and 5 could, without limitation, be copper, tungsten, chromium, stainless steel, nickel, nichrome, titanium, gold, silver, brass, platinum, iridium, platinum-iridium or any alloy of these, or any other conducting material. However, in some embodiments, the ferromagnetic materials may be minimized to reduce the potential interference with MRI diagnostics and because of magnetic attraction forces between the injectable and the magnetic field generator. The stimulating electrode diameter or maximum cross-sectional dimension that is in the range of 0.5 and 1 mm, 1 mm and 2 mm, or 2 mm and 3 mm, and its length may be less than 0.5 mm, 0.5 mm and 1.0 mm, or 1.0 mm and 2.0 mm. The return electrode may have the same diameter and the same or larger length. A larger surface area for the return electrode versus the stimulating electrode may reduce its current density and can, in some embodiments, reduce the likelihood or prevent it from inadvertently stimulating another nearby nerve, axon, or neuron. Although the exposed ends 4a and 5a of the electrodes 4 and 5 in FIG. 1 are depicted with flat ended surfaces, one or both exposed ends of the electrodes may comprise a semispherical configuration, and/or a tapered configuration, for example. The encapsulated ends 4b and 5b of the electrodes 4 and 5 are also depicted with the same cross-sectional dimension as the rest of the electrodes 4 and 5, but in other embodiments, the encapsulated ends may comprise a reduced cross-sectional dimension such that the encapsulating material can maintain a uniform outer diameter or cross-sectional dimension and shape about the electrodes. FIG. 4c, depicts such an embodiment of an injectable 495, with a stepped change in dimensions between the exposed 401, 403 and encapsulated portions 405, 407 of each electrode 409 and 411 (diode and inductor not shown), but in other examples, the transition between the exposed and encapsulated portions may be gradual or tapered. The encapsulation material 413 could be partially or completely coated or insulated with PTFE (polytetrafluoroethylene), PET (polyethylene terephthalate), nylon, silicone, polyethylene, polyurethane, latex, polyimide, BoPET (biaxially-oriented polyethylene terephthalate), any mixture or combination of these, or other suitable insulator to protect the conductor from corrosion and/or to prevent the surrounding tissue from reacting adversely. The thickness of the insulation is typically 5 to 500 microns, thick enough to resist or avoid pinholes, scratches, or tears, but also thin enough to allow passage through a syringe or other injection device. The exposed conducting portion of the injectable conductor may be coated or plated with yet another conducting material is that more compatible with bodily tissue. In FIG. 1, the injectable 199 is depicted with an encapsulation material 8 that has an overall oblong shape, but in other examples, such as in FIG. 4c, the outer dimensions of the encapsulation material 413 may be generally uniform along its longitudinal length, and/or the outer dimensions of the encapsulation material 413 may be generally the same or flush with the outer dimensions of the exposed portions 401, 403 of the electrodes 409, 411 at their interfaces 413, 415, as shown in FIG. 4c. In another example depicted in FIG. 4d, one or both of the electrodes 420, 422 can have a uniform diameter, and the encapsulation material 424 can also have a uniform diameter larger than the diameter of either electrode 420, 422. In FIG. 4d, the end surface 426 of the stimulating electrodes 420 is flush with the end 430 of the encapsulating material 424 and therefore only the end surface 426 is exposed, while a length of return electrode 422 extends a distance from the end 432 of the encapsulating material 424 by up to 0.5 mm, 1 mm, 2 mm, 3 mm or 4 mm, for example. In other examples, the stimulating and/or return electrodes are both flush or protruding, or the stimulating electrode may protrudes and the return electrode is flush. In some further embodiments, the exposed length or surface area of the return electrode is greater than the exposed length or surface area of the stimulation electrode.

I other examples, the injectable 491 could have multiple strands 434 at one or both ends 436, 438 to stimulate multiple locations simultaneously as shown in FIG. 4e, or multiple injectables could be injected. Without limitation, some or all of these strands 434 could flare out after placement inside the body and also to help keep the injectable 491 anchored or positioned over a long period of time and during bodily motions. The injectable 489 may also comprise an expandable structure 440, such as a lattice or mesh, in a reduced profile or compressed configuration 440a during delivery of the injectable 489 as shown in FIG. 4f, and then increases in volume or size into enlarged profile or expanded configuration 440b after injection as shown in FIG. 4g. In FIGS. 4f and 4g, the mesh 440 decreases in its longitudinal dimension as it expands its cross-sectional area or dimension, but in other examples, a non-shortening expandable helix design may be used, e.g. the helical structure taught in US Pub. 2006/0079955. The expansion of the mesh 440 may result from the resilient properties, shape-memory, or pseudo-elastic phase changes in the mesh material. Without limitation, the injectable could have other spring-loaded components that help anchor the injectable in the body and reduce or prevent migration after placement. Some treatments require multiple nerves, nerve fibers, or neurons to be stimulated simultaneously. For example, one muscle may require many nerve fibers to be stimulated to achieve full muscle movement. In the brain, often many locations need stimulation to treat a general disorder like anxiety or dementia. In these cases, multiple strands of conductors on a single injectable or multiple injectables could be placed, and one stimulator coil could stimulate all of them or multiple stimulator coils could be used.

A number of parameters of the individual components of FIG. 1 may affect the efficiency of stimulation, which in turn, may affect battery size and cost of the. Because this system relies on very high currents and voltages appearing for short periods of time, the resistances and/or voltage drops in the path from the battery 31 to ground 34 in FIG. 1 should be reduced or minimized. These include the internal resistance of the battery 31, the resistance of the coil 9, the equivalent series resistance of the capacitor 32, the voltage drop across the rectifier 33, and the on-resistance of the MOSFET 30. Although not shown in FIG. 1, a power capacitor is typically employed in parallel with the power source or battery 31, and this power capacitor should also have a low equivalent series resistance. In many cases, these resistances are a function of frequency, and care should be made to examine these losses up the resonant frequency between the capacitor 32 and the coil 9.

FIG. 1 further shows the multiple exemplary relative orientations 60, 61, 62, 63, 64 that injectable 2 may have relative to the coil 9 and the surface of the body 3. The injectable 199 may be oriented along the direction of the magnetic field generated by wearable coil 9, producing a strong inductive coupling. The relative orientation of the injectable 199 can vary a full 90 degrees in FIG. 1, but the lateral position of the wearable coil may need to shift to achieve optimum coupling. For example, the injectable may be parallel to the coil windings at orientations 60 and 64. Or, the injectable may flare out at an angle relative to the plane of the coil in injectable orientations 61 and 63. Or, the injectable may be perpendicular to the coil in injectable orientations 62.

Figure 3:
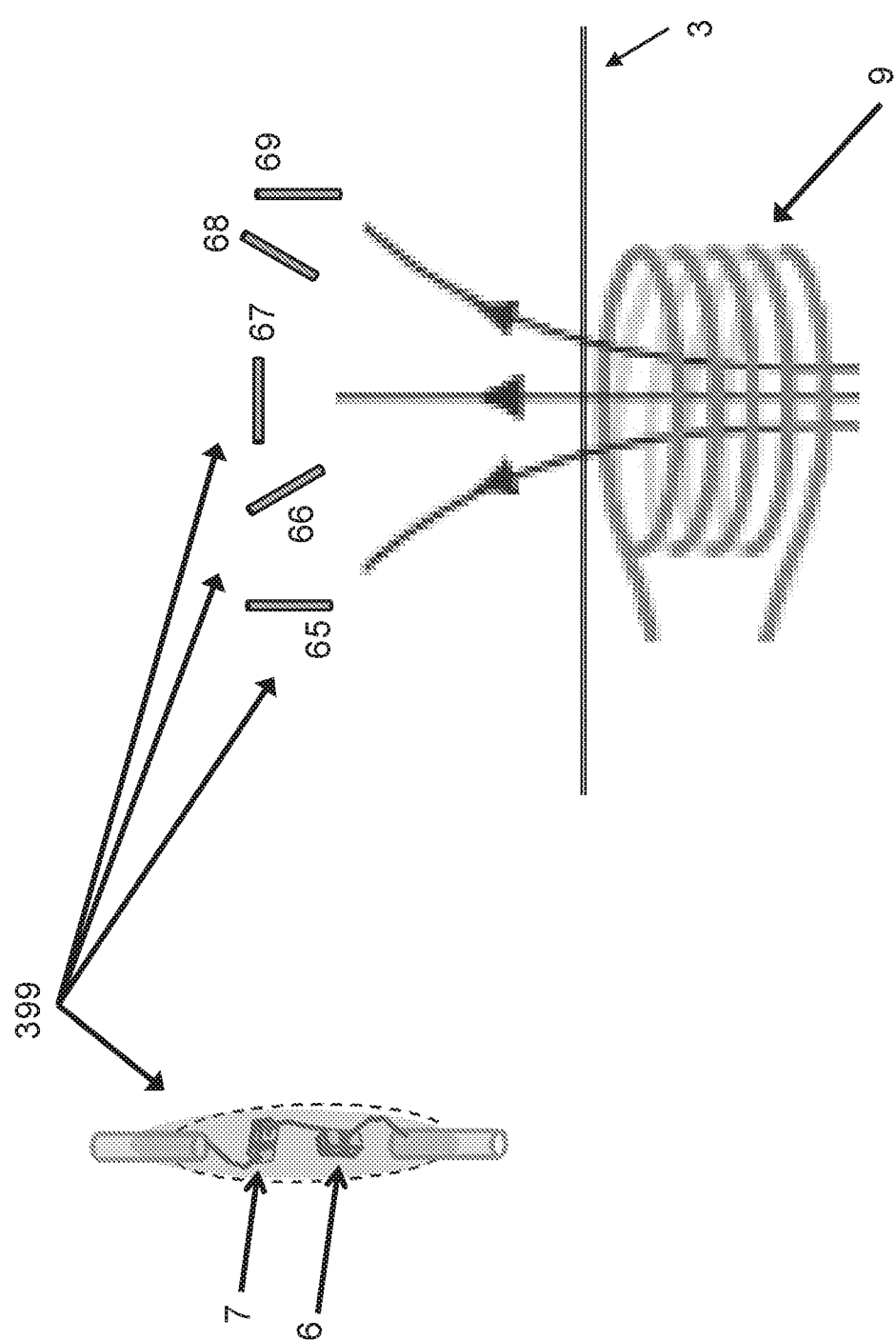
FIG. 3 is a graphical representation of an alternative orientation of the inductor windings in the elongate injectable and the corresponding direction of the magnetic field produced by the wearable field generator.

Another way to achieve alignment is shown in FIG. 3, with the inductor coil 9 is to provide an injectable 399 where the orientation of the inductor 7 in the injectable is perpendicular to the long dimension or longitudinal axis of the injectable 399, such that the injectable 199 is oriented parallel to the windings of the wearable coil 9. The variety of relative orientations of the injectable 199 to the coil 9 illustrated in FIG. 1 and FIG. 3 provides many embodiments for mounting, placing, and orienting both the injectable and the wearable, allowing for optimization of the multitude of neural stimulation applications. For example, the injectable may be parallel to the coil windings in injectable position 67. Or, the injectable may flare out at an angle relative to the plane of the coil in injectable positions 66 and 68. Or, the injectable may be perpendicular to the coil in injectable positions 65 and 69. In some examples, the treatment kit comprises a plurality of different injectables, with one or more injectables with a parallel orientation of the inductor and one or more injectables with a perpendicular orientation of the inductor, and selecting the type of inductor based on the relative orientation of the adjacent skin surface, the direction of the implantation to the treatment site.

Without limitation, multiple injectables with inductor windings oriented as exemplified in FIG. 1 or FIG. 3 could allow stimulation at multiple sites by the same wearable. For example, one wearable could activate two injectables as shown in injectable locations 61 and 63 in FIG. 1, each injectable with its inductor windings aligned with the wearable's magnetic field, but one injectable is adjacent to one nerve and the other is adjacent to another nerve. Further by example, bilateral stimulation of both hypoglossal nerves by one wearable for treatment of obstructive sleep apnea could provide benefits over unilateral stimulation. In this example, the attending physician would inject two injectables into locations 61 and 63 in FIG. 1, and then mount the wearable coil 9 between the two hypoglossal nerves, which are symmetrically located on either side of the throat or neck.

The benefits of multiple injectables and multiple field generators wherein subsets of injectables are activated by one field generator or by subsets of multiple field generators can be applied to multiple situations. One situation is applications where the exact location for stimulation is unknown, and multiple injectables are placed to cover are larger area, possibly with each addressable by orientation of the injectables with the field generator. Another is applications where multiple stimulations are required in dense areas of neurons, such as the brain, or dense areas of nerves, such as the spinal cord. Still another is applications wherein the body experiences physiological or neurological changes over time, and the stimulation treatment is to adjust or re-optimize. For example, these changes could be due to plasticity. Or, these changes could be due to evolution of the disease state over time from degeneration, physiological or neurological reaction, or natural adaptation, aging, or other evolution.

FIG. 4a shows the injectable 497 comprising two inductors 7, each connected in series and oriented the same way as the single inductor 7 in FIG. 1. A diode is provided between the inductors 7 and the stimulating electrode 4. With this configuration, twice the amplitude of the induced voltage is achieved at the electrodes 4, 5 of the injectable 497, and the packaging is kept long and thin. Higher inductance (more coil turns in total) of these inductors produces higher stimulation amplitudes. Without limitation, a longer coil with more turns and the same diameter can accomplish the same advantage of multiple serial coils. Inductances as high has 1.0 millihenry are available from Taiyo Yuden as part number CBC3225T102KR, wherein side dimensions are less than 3 mm, and therefore fit into an injectable. Without limitation, the injectable may also include 3, 4, 5, 6 or more inductors arranged in a linear fashion to achieve greater stimulation amplitude, lower power from the battery, deeper penetration, or a combination if these.

FIG. 4b depicts an injectable 499 containing no inductors and only one diode 6. In this case, the injectable can be much smaller in diameter and length, as diodes are available in very small packages less than 1 millimeter in all dimensions. However, this configuration without the inductors generates the lower voltage amplitude at the electrodes 4, 5. Nevertheless, some application like deep brain stimulation can be achieved with these lower voltages, as no myelin layer insulates the electrical path from the electrode to the neurons.

Stimulator-Body Configurations

One exemplary embodiment of this neural stimulation system is shown schematically in FIG. 2a and comprises an external packaged wearable field generator 298 that may be coupled to the external or skin surface 19 of the patient, and an internal or implanted injectable 2 portion that concentrates the field of the wearable field generator 298 to activate only a targeted nerve or small group of neurons or group of nerve fibers. The packaged wearable field generator 298 may comprising a housing containing a processing or computer unit to generate the drive signals to the stimulator coil 9 in FIG. 1 and to receive input to allow for adjustments in stimulation parameters from the user or healthcare provider, either directly through an input interface on the housing of the device, and/or via an interface to a smartphone or other device, over a WiFi, Bluetooth, RFID, or similar network or wireless protocol, at the location of the user or from a remote location. This embodiment may also include base station 3 that communicates with packaged wearable field generator 298 and with an external network LAN, WAN, WiFi, Cloud or other type of network. Without limitation, the packaged wearable field generator 298 could be activated or configured in response to data sensed by its own sensors, other body sensors, or sensors in the base station 3. For example, a plethysmography sensor could be mounted on the portion of the housing of the wearable field generator 298 configured to face the skin surface 19, and further configured to sense breathing and to notify the user and/or to automatically activate the stimulation during inhaling for patients with Obstructive Sleep Apnea. Furthermore, this sensed data can be made available to the attending nurse or physician or can be accumulated in a central database with other patient data to improve the product or general scientific understanding over time. The base station 3 can also contain a wireless or wired charging system for the packaged wearable field generator 298 or serve as the vehicle for programming by the physician when the device is deployed after diagnosis or is maintained at follow-up visits. In some variations, the stimulation coil of the wearable field generator may be used to charge the wearable field generator and/or to transmit data to the base station. The base station may optionally comprise a cavity in which the wearable field generator may be placed for charging and/or data collection. The injectable 2 shown in FIG. 2b may be placed with a syringe 42 or other injection system and be guided to the proper location by instantaneous imaging. This imaging could be magnetic resonance imaging (MRI), X-Ray imaging, ultrasound, fluoroscopy, or other body imaging system.

Wearable Coil Designs

Coil 9 in FIG. 1 may be wire-wound coil or a flat coil made from either a rigid or flexible circuit board. The diameter of the coil should be between 1 and 40 cm and large enough for penetration depths of 1 to 10 cm, possibly etched on a circuit board. For a rigid circuit board, the material could be the industry standard FR4, or could be glass, or hard plastic with a thickness between 0.5 mm and 2.0 mm, with the smallest thickness for 1-2 cm diameter coils and the larger thickness for 10-40 cm diameter coils. For a flexible circuit board, the flexible material could be the industry standard polyimide, or could be BoPET, polyethylene, polyurethane, nylon or PTFE. The material is selected to achieve the flexibility to follow the contour of the skin, but strong enough to be durable after multiple applications of the stimulator. The thickness of the flexible material is between 12.5 and 200 microns for 1 to 40 cm diameter coils, as smaller coils are supportable by thinner circuit boards.

Figure 12E:
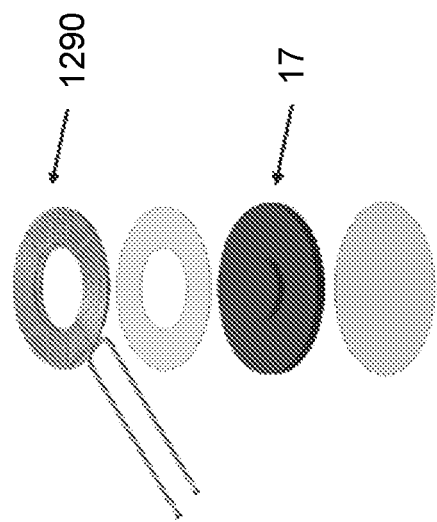
Figure 12D:
Figure 12C:
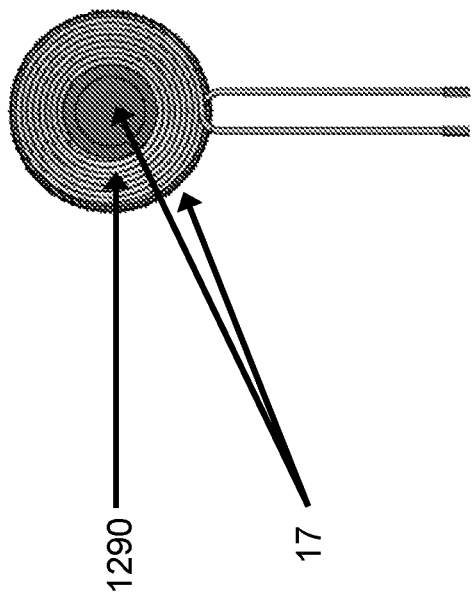
FIG. 12c is a top-view drawing of an exemplary coil for the wearable of FIG. 12b for hypoglossal nerve stimulation.

A flat, magnetically permeability material, such as ferrite, can be added to the back of and/or fill the hole in the coil 9 in FIG. 1, the back side not facing the body, as shown by 17 in FIG. 12c and FIG. 12e for exemplary coil 1290, to increase the magnetic field strength and hence provide higher stimulation at the injectable. Adding this material may also reduce the power consumption of the wearable needed for stimulation, especially if the high-permeability material is not electrically conductive. To reduce the electrical losses in the coil due to eddy currents, coil 9 of FIG. 1 could wound from stranded wire wherein each strand is insulated.

Wearable Housing

The wearable field generator 298 in FIG. 2a at least the stimulator coil, which is facing the body and positioned as close as possible to the injectable conductor. The battery and driver circuit may be combined with the stimulator coil into one unit as shown with a battery 15 and a driver circuit 16 in FIG. 12b, or these may be carried separately in a more convenient location. The configuration in FIG. 12b comprises a multi-layer assembly comprising a flattened or planar configuration and may have a circular, rectangular square or other shape. In some embodiments, the driver circuit fits into the center hole of the spool containing the windings of the simulator coil. This assembly is fully enclosed in a hard or partially flexible plastic housing 13, as shown in FIG. 12a. The thickness of the housing may be provided to reduce or minimize the distance from the coil windings to the injectable, but thick enough to be strong and uncompromised when dropped or after normal use or normal misuse. A contact sensor in the housing can turn the system off when not placed against the skin to save battery life and to prevent physical vibration of nearby ferromagnetic objects.

In FIG. 2a, the wearable field generator 298 is attached to the body by straps, elastic bands, hook and loop fasteners, buckles, adhesives, pins, or similar mechanism, with the stimulator coil(s) facing the skin. FIG. 12a depicts the housing 13 of the coupled to an adhesive ring 14 for attachment to the skin. Alternatively, the wearable portion may be attached to clothing or other attire using pockets, clamps, pins, adhesives, Velcro, or other suitable attachment means. Within the clothing or attire, the appropriate location of the wearable portion depends on the location and type of stimulation.

The coil and driver circuit assembly should be mounted snugly against the body using the aforementioned attachment methods, as the stimulation intensity will vary with the distance between the injectable and the coil windings. If the battery is not contained in this assembly, then wires are routed to the battery's location to bring power to the coil and driver circuit assembly.

Injection System and Method

FIG. 2b illustrates one embodiment of a delivery system for the injectable 199. In this embodiment, the injectable is provided at the point-of-manufacture within a syringe 42 for delivery through a hollow needle 43 to the appropriate position to be stimulated. In other examples, the injectable 199 may be loaded into the syringe 42 at the procedure site. Although a syringe device is depicted, in other examples, the implantation site may be accessed using a guide wire and/or an introducer, and the injectable 199 may be loaded or pre-loaded into a catheter or other delivery cannula. A longer cylinder or plunger 41 such as nylon thread or elongate push member, preferably non-conducting, and selected with sufficient column strength and a similar diameter is pushes the injectable 199 through the needle 43 until the injectable 199 is near the end of the needle. The injectable is injected into the body, guided or pre-determined by an X-ray, fluoroscopy, CT, MRI, ultrasound, endoscopy or other real-time imaging system, until the tip of the needle is at the stimulation location. Then, a hand or mechanical gripper pushes the plunger 41 in FIG. 2b of the syringe 42, which pushes the injectable 199 out of the needle 43. Once the injectable is pushed to the desired location the Plunger 41 in FIG. 2a is backed out by the gripper, and then the syringe 42 and needle are withdrawn, leaving the injectable 199 in place. In some embodiments where the injectable needs to be stimulated and the stimulation response observed to help guide the injectable to the target location, the wearable portion could be mounted nearby and activated during the injection. Without limitation, the needle could be preloaded with one or more injectables and each one placed sequentially into nearby locations, and the injectable system be part of a kit and delivered in a sealed and sterile package. The needle would range in size from 14 gauge (1.6 mm inside diameter) for 1 cm deep neural stimulations to 9 gauge (3.0 mm inside diameter) for 10 cm deep neural stimulations, as indicated in the later examples. The needle cavity may also contain a biocompatible liquid carrier gel, liquid or lubricant.

Wearable Installation and Calibration

Once the injectable is in the appropriate location, the wearable field generator portion is mounted as it will be worn by the patient. The intensity of the stimulation is increased by slowly increasing the supply voltage to the driver circuit 31 in FIG. 1 or by increasing the pulse width 35 in FIG. 1. When the desired amount of stimulation is achieved, that voltage level is noted by the controller portion of the driver circuit. If appropriate, the attending physician will then specify a range of voltages around this level that the patient is able to set without supervision. If not appropriate, the patient will have a stimulation that was fixed by the physician, and cannot be changed without the physician present. If the patient does have ability to change the stimulation parameters, these can be accomplished through a smart phone, base station 3 in FIG. 2a or similar interface. Without limitation, the patient or attending physician could also have the liberty of adjusting the burst frequency in addition to the voltage level, each burst being a repeated sequence of rectified and decaying resonant pulses. The desired amount of stimulation or other parameter could, depending on the nature of the treatment and the ability of the patient, be determined by feedback from patient or calibrated to a reference level based on feedback from other electrical signals in the body such as EKG, EMG, or other signal, or to another reference level pre-determined to be effective in a clinical trial. For example, EMG signals from healthy and connected muscles could be used to recruit and stimulate nerves connecting other muscles in the same muscle group that are unconnected due to pathology or injury.

Temporary and Permanent Installation

The methods just described can allow the patient to experience treatment with the neural stimulator active for a trial period, if desired. After the trial period, the patient and the attending physician will determine if the neural stimulator should be adjusted, terminated, or the injectable repositioned. Stimulation parameter adjustments can be made by re-using the feedback methods described for initial settings. If termination is desired, then the patient can likely continue a normal life with the injectable in its current location, but not activate it with the wearable portion. The inactivated injectable is not expected to cause complications in normal living or during MRI, X-ray, or other normal diagnostic procedure or other incidental exposure to magnetic fields. If the injectable is causing complications or the patient or physician wants it removed for another reason, then it can be removed using methods and tools that are used for a biopsy or removing cancerous tissue, such as keyhole surgery, guided by imaging such as functional MRI and/or ultrasound. If the injectable conductor needs to be repositioned, then another one could be placed downstream or upstream along the nerve pathway of the nerve to be stimulated, leaving the first injectable in place. Or, the first injectable may be removed and another one injected.

Figure 2C:
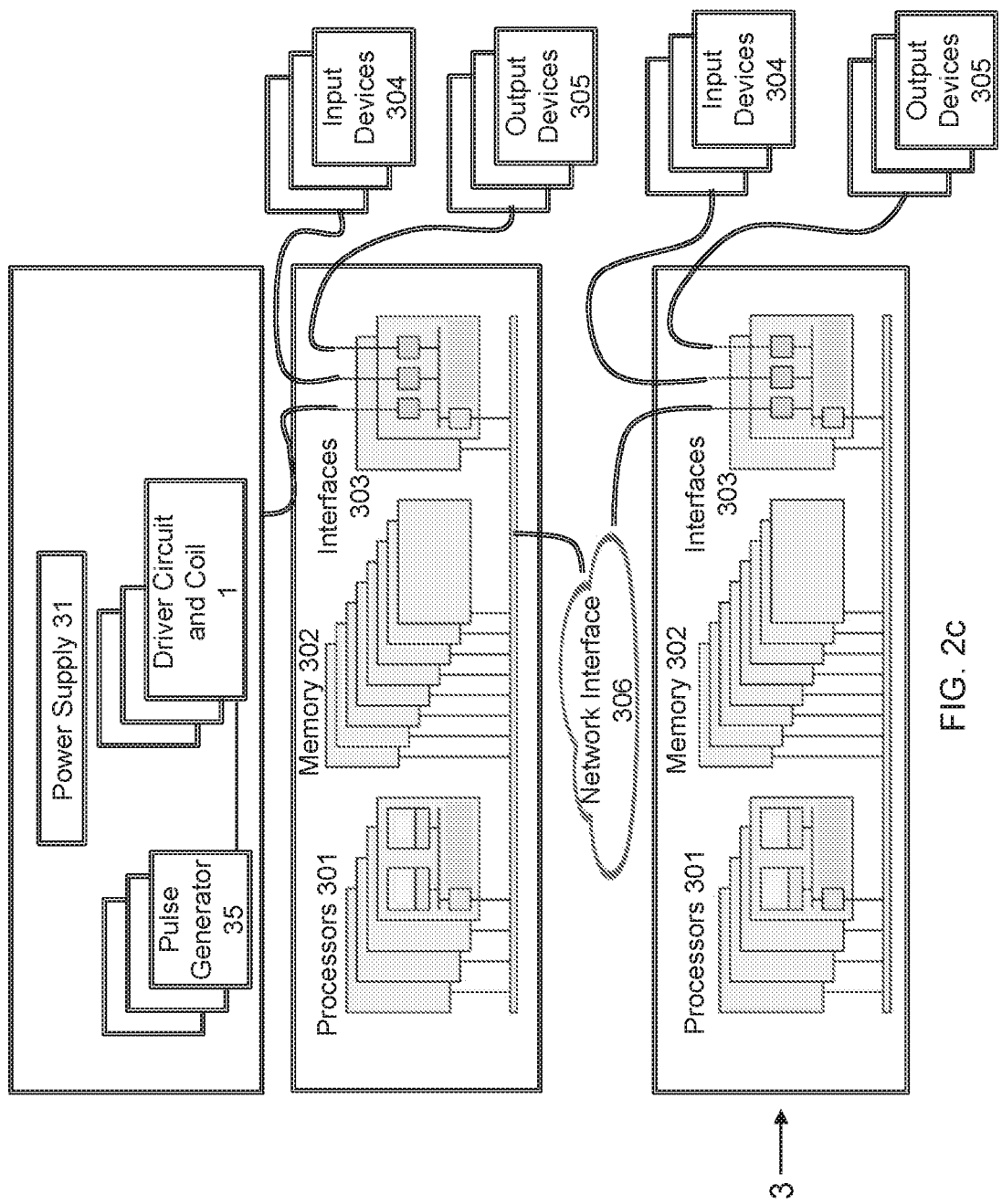
FIG. 2c is a graphical representation of the data computing, data storage, and data communications functions present in the wearable or the base station.

As noted previously, the packaged wearable field generator 298 in FIG. 2a or the base station 3 in FIG. 2a, or both of these, may comprise a data processing device as illustrated in FIG. 2c, which in turn may comprise a controller connected to one or more stimulation coils. The controller may comprise one or more processors 301 and one or more machine-readable memories 302 in communication with the one or more processors. The processor 301 may incorporate data received from memory 302 and operator input 304 to control the processing device. The inputs 304 to the controller may be received from one or more machine generated and/or human generated sources (e.g., user input). The memory 302 may further store instructions to cause the processor to execute modules, processes and/or functions associated with the processing device, such as the method steps described herein. The processor 301, memory 302, and interfaces 304 and 305 may be local to the wearable device 298 or the base station 3 or at a remote computing facility in communication with the wearable over a network interface.

The controller may be implemented consistent with numerous general-purpose or special purpose computing systems or configurations. Various exemplary computing systems, environments, and/or configurations that may be suitable for use with the systems and devices disclosed herein may include, but are not limited to software or other components within or embodied on personal computing devices, network appliances, servers, or server computing devices such as routing/connectivity components, portable (e.g., hand-held) or laptop devices, multiprocessor systems, microprocessor-based systems, and distributed computing networks. Examples of portable computing devices include smartphones, personal digital assistants (PDAs), cell phones, tablet PCs, phablets (personal computing devices that are larger than a smartphone, but smaller than a tablet), wearable computers taking the form of smartwatches, portable music devices, and the like, and portable or wearable augmented reality devices that interface with an operator's environment through sensors and may use head-mounted displays for visualization, eye gaze tracking, and user input.

Processor

Referring still to FIG. 2c, the processor 301 may be any suitable processing device configured to run and/or execute a set of instructions or code and may include one or more data processors, image processors, graphics processing units, physics processing units, digital signal processors, and/or central processing units. The processor 301 may be, for example, a general-purpose processor, Field Programmable Gate Array (FPGA), an Application Specific Integrated Circuit (ASIC), and the like. The processor may be configured to run and/or execute application processes and/or other modules, processes and/or functions associated with the system and/or a network associated therewith. The underlying device technologies may be provided in a variety of component types, e.g., metal-oxide semiconductor field-effect transistor (MOSFET) technologies like complementary metal-oxide semiconductor (CMOS), bipolar technologies like emitter-coupled logic (ECL), polymer technologies (e.g., silicon-conjugated polymer and metal-conjugated polymer-metal structures), mixed analog and digital, and the like.

Memory

In some variations, the memory 302 depicted in FIG. 2c may include a database and may be, for example, a random access memory (RAM), a memory buffer, a hard drive, an erasable programmable read-only memory (EPROM), an electrically erasable read-only memory (EEPROM), a read-only memory (ROM), Flash memory, and the like. As used herein, database refers to a data storage resource. The memory 302 may store instructions to cause the processor to execute modules, processes and/or functions associated with the processing device, such as ECG signal data processing, communication, display, and/or user settings. In some variations, storage may be network-based within a remote portion and accessible for one or more authorized users. Network-based storage may be referred to as remote data storage or cloud data storage. Historical usage or physiological signal data stored in cloud data storage (e.g., database) may be accessible to respective users via a network, such as the Internet. In some variations, database may be a cloud-based FPGA.

Some variations described herein relate to a computer storage product with a non-transitory computer-readable medium (also may be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also may be referred to as code or algorithm) may be those designed and constructed for a specific purpose or purposes. Examples of non-transitory computer-readable media include, but are not limited to, magnetic storage media such as hard disks; optical storage media; holographic devices; magneto-optical storage media such as optical disks; solid state storage devices such as a solid state drive (SSD) and a solid state hybrid drive (SSHD); carrier wave signal processing modules; and hardware devices that are specially configured to store and execute program code, such as Application-Specific Integrated Circuits (ASICs), Programmable Logic Devices (PLDs), Read-Only Memory (ROM), and Random-Access Memory (RAM) devices. Other variations described herein relate to a computer program product, which may include, for example, the instructions and/or computer code disclosed herein.

The systems, devices, and/or methods described herein may be performed by software (executed on hardware), hardware, or a combination thereof. Hardware modules may include, for example, a general-purpose processor (or microprocessor or microcontroller), a field programmable gate array (FPGA), and/or an application specific integrated circuit (ASIC). Software modules (executed on hardware) may be expressed in a variety of software languages (e.g., computer code), including C, C++, JAVA*, Python, Ruby, VISUAL BASIC*, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. Additional examples of computer code include, but are not limited to, control signals, encrypted code, and compressed code.

User Interface

A user interface may permit an operator to interact with and/or control the processing device directly and/or remotely. For example, the user interface may include an input device 304 for an operator to input commands and an output device for an operator and/or other observers to receive output (e.g., view patient data on a display device) related to operation of the processing device.

User interface may serve as a communication interface between an operator and the processing device. As shown in FIG. 2c, in some variations, the user interface may comprise an input device 304 and output device 305 (e.g., touch screen and display) and be configured to receive input data and output data from one or more of the wearable portions, computing devices, input device, and output device. For example, physiological signal data generated by another device may be processed by processors within wearable portion or remote portion and displayed by the output device (e.g., monitor display). As another example, operator control of an input device (e.g., joystick, keyboard, touch screen) may be received by user interface and then processed by controller for user interface to output a control signal to one or more of the processing device.

Output Device

As shown in FIG. 2c, an output device 305 of a user interface may output historical or physiological signal data corresponding to a user, and may comprise one or more of a display device and audio device. The display device may be configured to display a graphical user interface (GUI). A display device may permit an operator to view a physiological signal data and/or other data processed by the controller or other device. In some variations, an output device may comprise a display device including one or more of a light emitting diode (LED), liquid crystal display (LCD), electroluminescent display (ELD), plasma display panel (PDP), thin film transistor (TFT), organic light emitting diodes (OLED), electronic paper/e-ink display, laser display, and holographic display.

An audio device may audibly output subject data, sensor data, system data, alarms and/or warnings. In some variations, an audio device may comprise at least one of a speaker, piezoelectric audio device, magnetostrictive speaker, and/or digital speaker. In some variations, an operator may communicate with other users using the audio device and a communication channel. For example, the operator may form an audio communication channel (e.g., VoIP call) with a remote operator, technician, and/or subject.

Input Device

Some variations of an input device 304 schematically depicted in FIG. 2c may comprise at least one switch configured to generate a control signal. For example, an input device may comprise a touch surface for an operator to provide input (e.g., finger contact to the touch surface) corresponding to a control signal. An input device comprising a touch surface may be configured to detect contact and movement on the touch surface using any of a plurality of touch sensitivity technologies including capacitive, resistive, infrared, optical imaging, dispersive signal, acoustic pulse recognition, and surface acoustic wave technologies. In variations of an input device comprising at least one switch, a switch may comprise, for example, at least one of a button (e.g., hard key, soft key), touch surface, keyboard, analog stick (e.g., joystick), directional pad, pointing device (e.g., mouse), trackball, jog dial, step switch, rocker switch, pointer device (e.g., stylus), motion sensor, image sensor, and microphone. A motion sensor may receive operator movement data from an optical sensor and classify an operator gesture as a control signal. A microphone may receive audio and recognize an operator voice as a control signal.

Network Interface

A processing device described herein may communicate with one or more networks and computing devices through a network interface 306. In some variations, the processing device may be in communication with other devices via one or more wired and/or wireless networks. For example, the network interface 306 may permit the processing device in wearable portion to communicate with one or more of a network (e.g., Internet), remote server, and database. The network interface may facilitate communication with other devices over one or more external ports (e.g., Universal Serial Bus (USB), multi-pin connector) configured to couple directly to other devices or indirectly over a network (e.g., the Internet, wireless LAN).

In some variations, the network interface 306 may comprise radiofrequency (RF) circuitry (e.g., RF transceiver) including one or more of a receiver, transmitter, and/or optical (e.g., infrared) receiver and transmitter configured to communicate with one or more devices and/or networks. RF circuitry may receive and transmit RF signals (e.g., electromagnetic signals). The RF circuitry converts electrical signals to/from electromagnetic signals and communicates with communications networks and other communications devices via the electromagnetic signals. The RF circuitry may include one or more of an antenna system, an RF transceiver, one or more amplifiers, a tuner, one or more oscillators, a digital signal processor, a CODEC chipset, a subscriber identity module (SIM) card, memory, and the like. A wireless network may refer to any type of digital network that is not connected by cables of any kind. Examples of wireless communication in a wireless network include, but are not limited to cellular, radio, satellite, and microwave communication. The wireless communication may use any of a plurality of communications standards, protocols and technologies, including but not limited to Global System for Mobile Communications (GSM), Enhanced Data GSM Environment (EDGE), high-speed downlink packet access (HSDPA), wideband code division multiple access (W-CDMA), code division multiple access (CDMA), time division multiple access (TDMA), Bluetooth, Wireless Fidelity (Wi-Fi) (e.g., IEEE 802.11a, IEEE 802.11b, IEEE 802.11g and/or IEEE 802.11n), voice over Internet Protocol (VoIP), Wi-MAX, a protocol for email (e.g., Internet Message Access Protocol (IMAP) and/or Post Office Protocol (POP)), instant messaging (e.g., eXtensible Messaging and Presence Protocol (XMPP), Session Initiation Protocol for Instant Messaging and Presence Leveraging Extensions (SIMPLE), and/or Instant Messaging and Presence Service (IMPS)), and/or Short Message Service (SMS), or any other suitable communication protocol. Some wireless network deployments combine networks from multiple cellular networks or use a mix of cellular, Wi-Fi, and satellite communication. In some variations, a wireless network may connect to a wired network in order to interface with the Internet, other carrier voice and data networks, business networks, and personal networks. A wired network is typically carried over copper twisted pair, coaxial cable, and/or fiber optic cables. There are many different types of wired networks including wide area networks (WAN), metropolitan area networks (MAN), local area networks (LAN), Internet area networks (IAN), campus area networks (CAN), global area networks (GAN), like the Internet, and virtual private networks (VPN). As used herein, network refers to any combination of wireless, wired, public, and private data networks that are typically interconnected through the Internet, to provide a unified networking and information access system.

Software Architecture

Because of the inductance of the stimulator coil 9 in FIG. 1, the driver circuit must be turned on sufficiently prior to the burst to allow needed current to build up in the coil. The time needed for this buildup is related to the time constant L/R, wherein L is the inductance of the coil and R is the resistance of the coil plus any other resistances in the path from the power supply to ground. The coil is turned on for enough time for current to build up, which is the build-up time. Then, the stimulator is turned off, allowing the stimulator coil 9 in FIG. 1 and the parallel capacitor to resonate, generating a decaying series of bi-phasic sinusoidal pulses. The stimulator stays off until it is time to start building up the current in the coil again prior to the next burst.

Examples

Figure 5B:
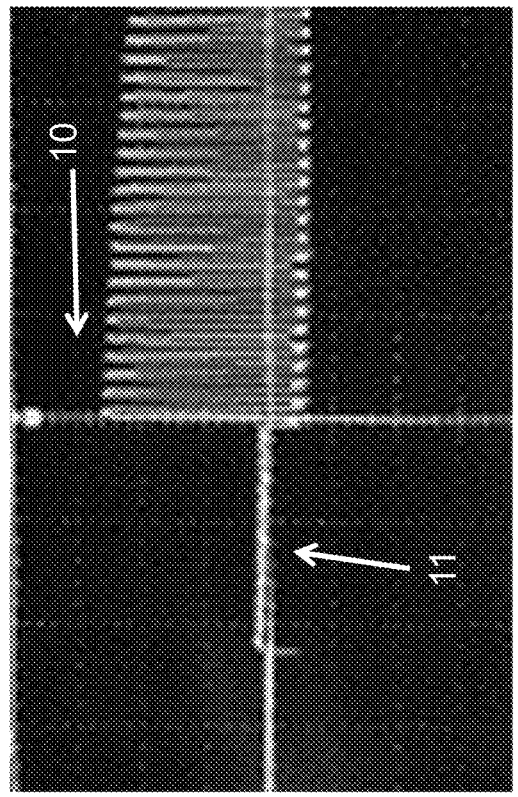
FIG. 5b shows an oscilloscope trace of the output of the elongate injectable of FIG. 1 for a longer time duration for energizing the wearable coil.
Figure 5A:
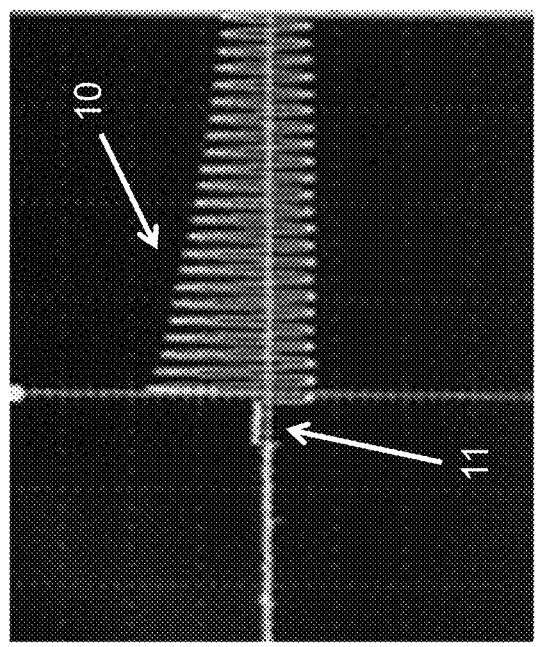
FIG. 5a shows an oscilloscope trace of the output of the elongate injectable of FIG. 1 for one time duration for energizing the wearable coil.

FIG. 5a and FIG. 5b show the voltage at a simulated injectable on an oscilloscope when the prototype driver circuit of FIG. 1 is driven by logic signal pulses at a rate of 50 per second. The horizontal time scale is 50 microseconds per division, and the vertical scale is 1 volt per division. In this case, the MOSFET 30 in FIG. 1 is turned on 30 microseconds prior to the centerline of the oscilloscope screen, and is turned off at the centerline. The current that built up in the coil is free to resonate with the parallel capacitor after the centerline. FIG. 5a shows that the simulated injectable presents a half-wave rectified sine wave voltage, initially at a 1.7 volt peak, then decaying slowly in amplitude. Hence, one electrode of the injectable can inject a single polarity of charge at the stimulation location. This charge will eventually polarize or depolarize a nearby nerve, neuron, or axon, achieving neural stimulation. The stimulation voltage can easily be increased by increasing either the supply voltage or by increasing the current buildup period in the coil. FIG. 5b shows a longer buildup time 130 microseconds of current in the coil, and a larger voltage amplitude appears at the injectable once the resonance begins. Hence, the amplitude of the stimulation is adjustable by the width of the stimulation input pulses 35 in FIG. 1. The voltage required for neural stimulation varies, but almost all stimulation therapies use voltages on the same order as achieved in FIG. 5.

FIG. 6a and FIG. 6b show an apparatus used to characterize the stimulator in FIG. 1, but where the injectable has a diode only as illustrated in FIG. 4b, wherein the electrical leads of the diode serve as the electrodes and an inductor is not provided. The saline bath (0.9% salt in water by weight) simulates the conductive tissue of the body. The injectable 499 includes a Schottky diode, part number MMBAT46-TR from Vishay, with lead wires connected to electrodes 4 and 5 for monitoring on an oscilloscope. The injectable 499 is aligned parallel with the windings of coil 690, as illustrated in FIG. 6a and FIG. 6b, and the conductive saline bath in the vinyl tub simulate the conductive tissue inside the body. The physical distance from the coil 690 to the diode 6 is about 1 centimeter. The power supply is providing 17 volts and 0.1 amps, and hence the wearable field generator for this configuration would consume 1.7 watts on average. The driver circuit is illustrated in FIG. 1 with details in FIG. 6d. The pulse generator 35 in FIG. 1 generated pulses at 32 Hz frequency, which is a typical burst frequency for neural stimulation. The pulse width 35 in FIG. 1 is 281 microseconds. FIG. 6c shows the results of the test apparatus of FIGS. 6a and 6b on an oscilloscope adjusted to 5 volts per division on the vertical scale and 8 microseconds per division on the horizontal scale. For each stimulation burst, monophasic voltage pulses of about 1.0 volts in amplitude. This voltage level is sufficient for some neural stimulations such as deep brain, but insufficient for others like peripheral nerves. FIG. 6d shows additional details of this example.

Figure 7A:
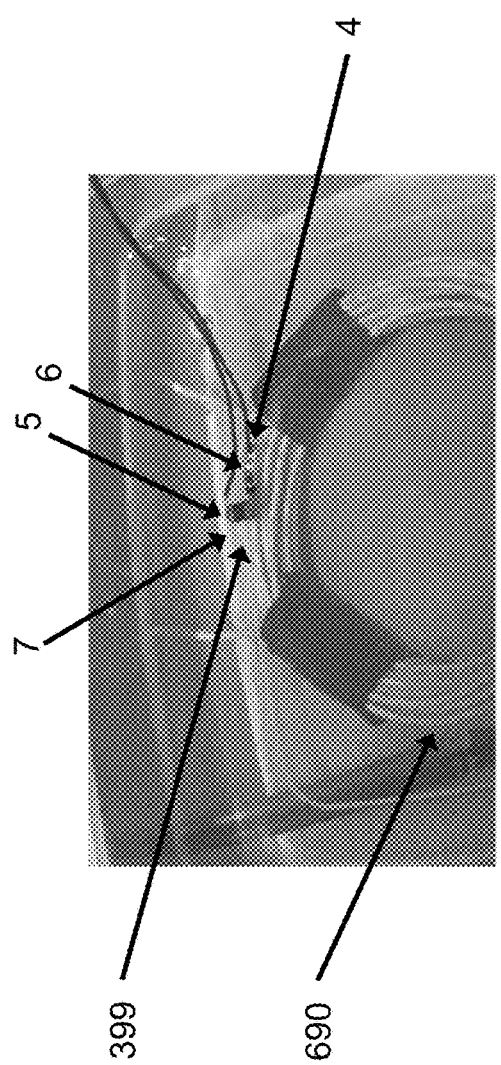
FIG. 7a shows the apparatus to test the output amplitude of the injectable placed in a saline bath that simulates human tissue for an embodiment wherein the elongate injectable contains one diode and one inductor, and the inductor is spaced above and its windings are oriented perpendicular to the windings of the wearable coil.
Figure 7C:
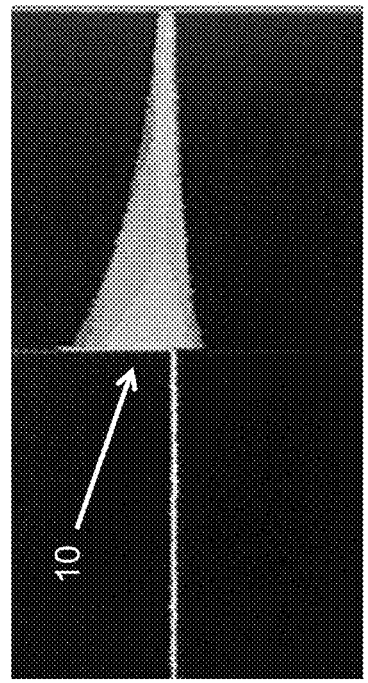
FIG. 7c is the oscilloscope trace of FIG. 7b with a different time scale.
Figure 7B:
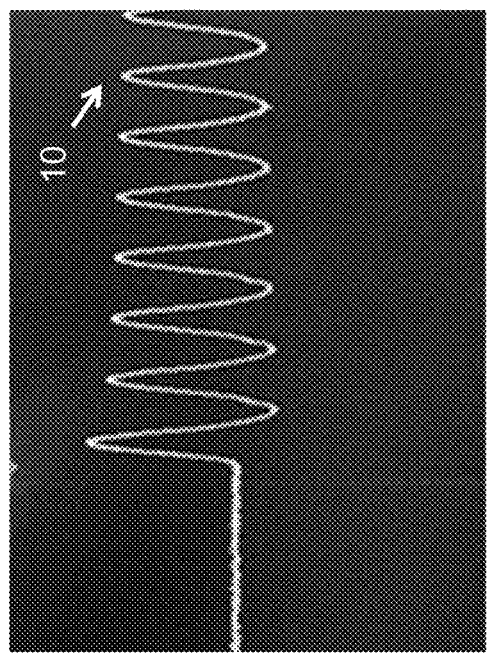

FIG. 7a shows the test apparatus of the injectable 399 with a 100-microhenry inductor 7, part number CBC3225T101MR from Taiyo Yuden, added in series with the Schottky diode 6, part number MMBAT46-TR from Vishay. The power supply of 1.7 watts and 281-microsecond pulses at 32 Hz to the wearable coil are the same as in the previous example. In FIG. 7a, note how the inductor 7 is oriented such that the magnetic field from the wearable coil 690 threads the windings of inductor 7, and the diode 6 is oriented to capture the signal induced in the single-turn of the saline bath as in FIG. 6b. The two electrodes 4 and 5 of the injectable 399 again have lead wires attached for measurement on the oscilloscope and have 2 square millimeters in exposed metallic surface area. Again the physical distance from the plane of the top of the coil 690 to the injectable 399 is about one cm. FIG. 7d shows additional details of the apparatus. FIG. 7b shows the results of the test apparatus of FIG. 7a on an oscilloscope adjusted to 5 volts per division on the vertical scale and 8 microseconds per division on the horizontal scale. Note that now the voltage amplitude at the two electrodes 4 and 6 of the injectable 399 in FIG. 7a in the saline bath is 10 volts in amplitude, which is sufficient for essentially all neural stimulations with a few square millimeters of exposed electrode surface area. Note also how this embodiment of adding the inductor and aligning its windings with the magnetic field of the wearable coil 9 generates a substantially stronger signal than the 1 volt amplitude of the diode only in FIG. 6c. FIG. 7c shows the results of the test apparatus of FIG. 7a on an oscilloscope adjusted to the same 5 volts per division on the vertical scale but now 80 microseconds per division on the horizontal scale. The test and device parameters used are provided FIG. 7d. The duration of the burst of pulses is several hundred microseconds, again covering the needs of most neural stimulation protocols.

FIG. 8a and FIG. 8b show the same apparatus used to test the same injectable as FIG. 7a, but now the injectable 399 is oriented so that its inductor windings are aligned with the magnetic field on center axis of the wearable coil 690, which is another location and orientation with strong magnetic field coupling. Again the physical distance from the plane of the top of coil 690 to the Injectable 399 is about one centimeter. FIG. 8c shows the results of the test apparatus of FIG. 8a and FIG. 8b and FIG. 8e on an oscilloscope adjusted to 10 volts per division on the vertical scale and 8 microseconds per division on the horizontal scale. FIG. 8c shows the resulting amplitude of pulses generated by the electrodes of the injectable 399 of FIG. 8a and FIG. 8b immersed in the saline bath. The peak amplitude is 10 volts. FIG. 8b shows the results of the test apparatus of FIG. 10 on an oscilloscope adjusted to same 10 volts per division on the vertical scale but now 80 microseconds per division on the horizontal scale. Again, the width of the burst is hundreds of microseconds, sufficient for most neural stimulation protocols. These results in FIG. 8c and FIG. 8d also indicate that the wearable coil could be made smaller, as smaller coils generate stronger magnetic fields at their center for stimulations of 1 cm of depth, like sleep apnea treatment. FIG. 8e provides the device parameters and test results.

FIG. 9a and FIG. 9b show a test apparatus to demonstrate a depth of penetration of 10 centimeters, which is the depth required for bladder control and spinal stimulation, and represents the maximum depth typically required for neural stimulation treatments. The injectable 999 has three 1.0 millihenry inductors, part number CBC3225T102KR from Taiyo Yuden, connected in series with a Schottky diode also in an SMT package, part number BAT46JFILM from ST Microelectronics. The total size of the injectable 999 was about 10 mm long and 2.5 mm diameter, so still easily injectable through a syringe, cannula or introducer. A 1000 Ohm resistive load was connected across the injectable to simulate the impedance of the saline bath or the human tissue. The wearable coil 990 was 13 centimeters in diameter, and the power supply was providing 1.6 watts to the driver circuit. The physical distance between the injectable 999 and the plane of the top of the wearable coil 990 was ten centimeters. FIG. 9c and FIG. 9d show the results of the test apparatus of FIG. 9a and FIG. 9b on an oscilloscope adjusted to 5 volts per division on the vertical scale and 8 microseconds per division on the horizontal scale. The voltage across the injectable has an amplitude of 5 volts, a pulse width of 16 microseconds, a burst frequency of 32 Hz, and a burst duration of hundreds of microseconds, which are the parameters typically needed for the deep neural stimulation therapies. FIG. 9d has additional details on the apparatus and results of this example.

Figure 10:
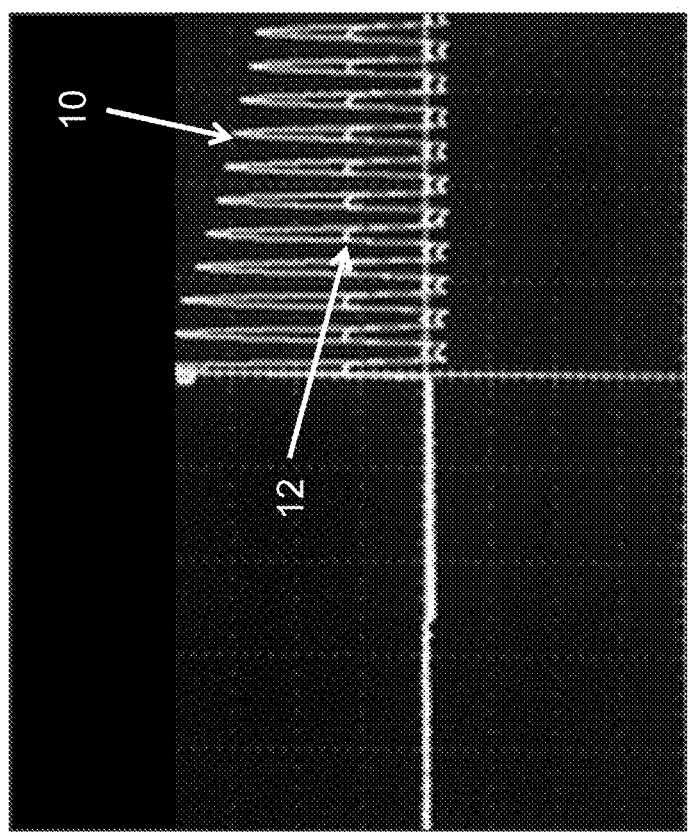
FIG. 10 shows two simultaneous oscilloscope traces, one where the elongate injectable contains a Schottky diode, and another where the injectable contains a Zener diode.

FIG. 10 shows the results of the test apparatus of FIG. 8a on an oscilloscope adjusted to 2 volts per division on the vertical scale and 25 microseconds per division on the horizontal scale. FIG. 10 shows the voltage 10 at the injectable using a Schottky diode, which does not limit the voltage, and on the same graph the voltage 12 using a Zener diode which does limit the voltage to 2.1 volts, which is a typical safe voltage level for neural stimulation when the electrode surface area is a few square mm.

Device Design for Obstructive Sleep Apnea Treatment

Figure 11:
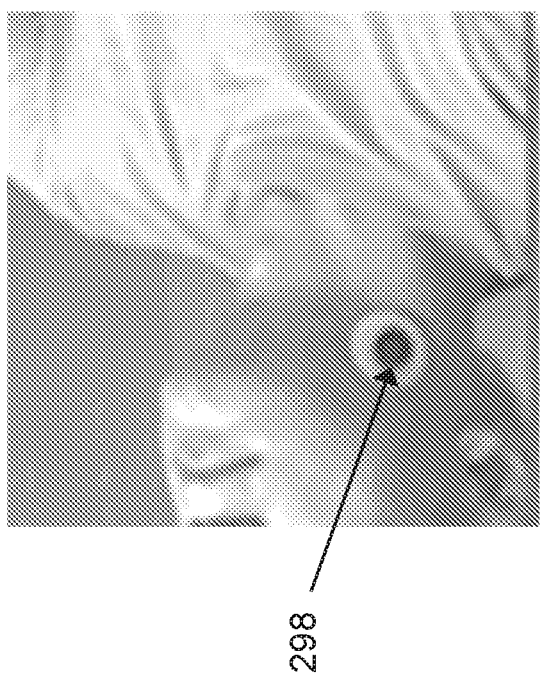
FIG. 11 is a view of a person wearing a mock-up of an embodiment of the wearable field generator at a location suitable for hypoglossal nerve stimulation.

FIG. 11 shows how the packaged wearable field generator 298 may be positioned and affixed onto the patient's neck or submandibular region near the hypoglossal nerve to relieve obstructive sleep apnea (OSA) during sleep. The resulting location is below and just forward of the ear, and underneath the jawbone, using the adhesive pad 14 FIG. 12*a*. This wearable is a mock-up only and adheres to the skin.

FIG. 12*a* shows the two parts of an embodiment of the wearable field generator 298 for sleep apnea treatment. The single-use adhesive pad or part 14 holds the permanent part or housing 13 against the skin. The single-use part is discarded after a night's use during sleep. The single-use part resembles the donut-shaped bandage that is commonly used for callouses but contains a non-allergic adhesive material that is comfortable for sleeping, and does not cause a skin reaction The adhesive part 14 may be pre-hydrated to prevent fluid absorption from the skin and leaves minimal marking on the skin when removed. The permanent part 14 contains the wearable field generator 298, and is an electronic device that activates the injectable, as described previously.

FIG. 12*b* shows the design details of the inside of the wearable's permanent part 13, which is an embodiment of the wearable field generator 298. In FIG. 12*b*, a rechargeable pack of button batteries 15 provides the power source 31 in FIG. 1. For example, the pack 15 could include three button batteries, each available from Renata as part number LMR 2016. In this example, the three batteries are connected in series as shown in FIG. 12*b* to provide a DC supply of 9 volts. When the permanent part of the wearable is not in use, the battery pack can be recharged by a base station 3 as depicted in FIG. 2*a*. For Obstructive Sleep Apnea, base station 3 is, for example, may be positioned the user's night stand. The charging of the batteries can take place either wirelessly or wired through a mating pair of connectors provided on the housing 13 of the wearable generator and the base station 3.

In FIG. 12*b*, a coil 1290 subassembly, with a ferrite core and backing 17, is used to generate the magnetic field described earlier. For example, the exemplary coil 1290 subassembly described in FIG. 12*c*, FIG. 12*d*, and FIG. 12*e* is available from TDK Corporation as part number WT202012-15F2-ID can be used for this part. In FIG. 12*b*, a circuit board 16 contains electrical components needed to operate the stimulator, including the rectifier 33, MOSFET 30, capacitor 32, and pulse generator 35 of the driver circuit of FIG. 1. FIG. 13 shows the details of the apparatus and test results for a prototype of a sleep apnea treatment embodiment using these components. The injectable procedure results in FIG. 13 achieves what is typically required for this treatment in pulse amplitude, burst duration, and burst frequency. The power consumption of 52 milliwatts in the wearable in FIG. 13 is sufficiently low for rechargeable button batteries to power the device for several hours during a night's sleep.

The circuit board in FIG. 12*b* may also contains one or more integrated sensors 51 that may include a microphone, plethysmograph sensor, a blood oxygen level sensor, or any combination of these.

In FIG. 12*b*, the coil subassembly 1290 is provided with an exemplary integrated sensor 51, such as Maxim Integrated as Part Number MAX30100. The sensor chip shines light from LEDs through the center-hole 44 in the ferrite layer 17 in FIG. 12*b*. This light passes through the patient's skin, and then reflects off the mandible bone or reflects off the injectable. The reflected light travels through the same hole 44 in the ferrite 17 to light sensor(s) in the integrated sensor 51. The signals from these light sensors are used to determine the patients' breathing, blood oxygen saturation level, and/or heart pulse rate. The blood oxygen saturation level is sensed by the ratio of red and infrared light reflected from the light source. The heart rate is sensed by the amount of light reflected through the volume of the blood flowing in the veins and arteries, as they enlarge and contract with heart beats.

How this sensor's outputs are used to sense the breathing cycle will be described next. Sensing the breathing cycle is critical for a hypoglossal nerve stimulator for relieving Obstructive Sleep Apnea. The stimulation is turned on just before inhalation, the airway opens, the patient inhales, and then the stimulation is turned off during exhalation, allowing the tongue muscles to rest and avoid fatigue.

The human heart rate increases during inhalation, and decreases during exhalation. This respiratory variation in heart rate is believed to be the result of changes in intrathorax pressure that increase cardiac filling and stroke volume during inspiration and reduce cardiac filling and stroke volume during expiration. The change in stroke volume would result in a change in blood pressure, but baroreceptor reflexes alter heart rate to maintain blood pressure. Hence, the plethysmography output frequency can directly sense and distinguish the inhaling phase vs. the exhaling phase, and to measure respiratory rate.

The oxygen content of the blood increases during inhalation and decreases during exhalation. Hence, the blood oxygen level sensor output amplitude can sense and distinguish the inhaling vs. the exhaling phase.

However, the direct measurement of plethysmography frequency or blood oxygen level amplitude from these sensors may optionally be combined with other sensing mechanisms. We will now describe three other sensing means: (1) envelope detection of the plethysmography sensor output, (2) amplitude of the microphone output, and (3) high-frequency content of the frequency spectrum of the microphone output.

Figure 14:
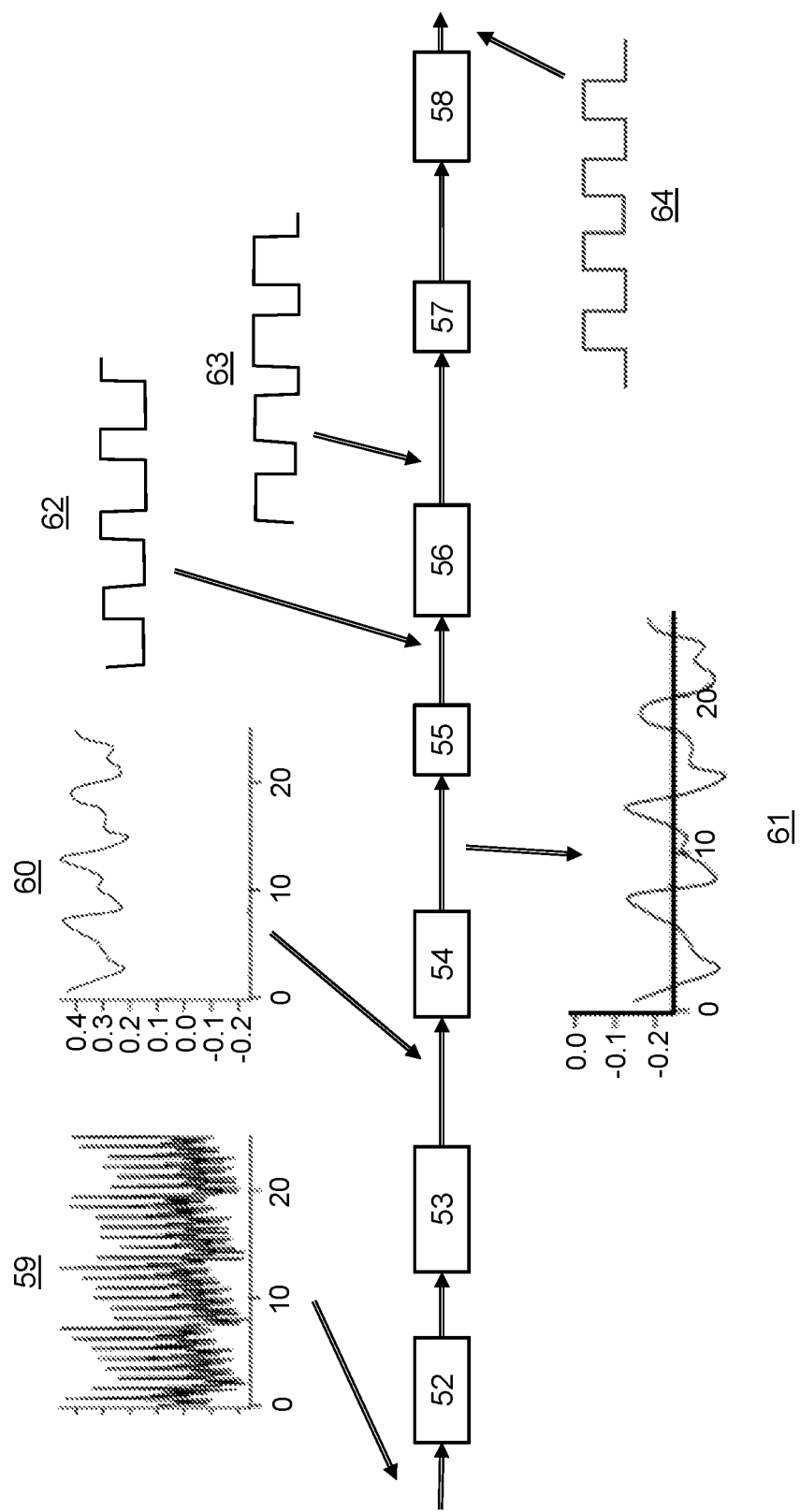
FIG. 14 shows a signal processing system, with an input from one of a plethysmograph sensor output depicted in FIG. 12b that ultimately produces a logic signal indicating when the patient is inhaling. This logic signal is useful for turning on stimulation of the hypoglossal nerve for a patient with Obstructive Sleep Apnea.

The input signal to function block 52 in FIG. 14 shows the expected plethysmograph sensor output 59 when mounted against the mandible as depicted in the wearable area of FIG. 11. The dominant feature of the waveform in all three cases is the heartbeat pulses. The breathing or ventilation cycle is represented by the envelope of the waveform input signal 60 to function block 52 in FIG. 14.

FIG. 14 depicts how the waveform from the sensor chip can be processed, using digital signal processing with the hardware described elsewhere herein, to reveal the patient's the breathing cycle. In this embodiment, the strongest periodic timing feature in the envelope output 60 of the sensor input 59 to 52 in FIG. 14 is the drop in the peak amplitude of the heartbeat pulses, and this peak occurs once for every breathing cycle. Hence, the signal processing algorithm of FIG. 14 will create a logic signal synchronized to this timing feature.

The first step in FIG. 14 is a local peak detector 52. The second step 53 provides interpolation between peaks. The third step 54 subtracts the average amplitude, centering the waveform 61 around zero. The fourth step 55 applies the SIGN function (logic level high when positive, low when negative) to generate the output 62. Next, an inverter 56 makes the desired synchronization points positive (rising) edges in the signal or data 63 in preparation for the following fixed-duration pulse generator 57, which generates a pulse at each rising edge. The length of the pulse is the optimized on-time of the stimulation for the inhalation phase. The final step is a time delay 58, which is the predetermined delay from the start of the synchronization point to the desired start of stimulation, which normally is just before the beginning of the inhalation phase. Because the breathing cycle is periodic, this time delay is expected to be the fraction of a period between the falling edge of the envelopes from 53 and the optimum point in time to start the stimulation. The end result of the signal processor in FIG. 14 is a logic signal 64 that turns on the hypoglossal nerve stimulation at the appropriate times to relieve Obstructive Sleep Apnea and turns it off the rest of the time to avoid muscle fatigue. In other examples, however, continuous activation may be provided, which may include sub-threshold and supra-threshold stimulation, as well as continuous supra-threshold stimulation.

Another method for detecting the breathing cycle for patients with obstructive sleep apnea employs a microphone sensor. FIG. 15a depicts an exemplary output of a microphone mounted in the wearable area, optionally after amplification, which may include an audible waveform 71 and a sound intensity level 72. These two signals are highly correlated with the air flow level 73 in the trachea, which was measured separately. Hence, a microphone mounted in wearable field generator of FIG. 12b is also likely to be indicative of the breathing cycle. The flow sound intensity 72 essentially disappears during obstructive events, as indicated in waveform 74 of FIG. 15b, and so the microphone signal can also detect when the patient is struggling to breathe and the effectiveness of the stimulation.

Figures 16A, 16B:
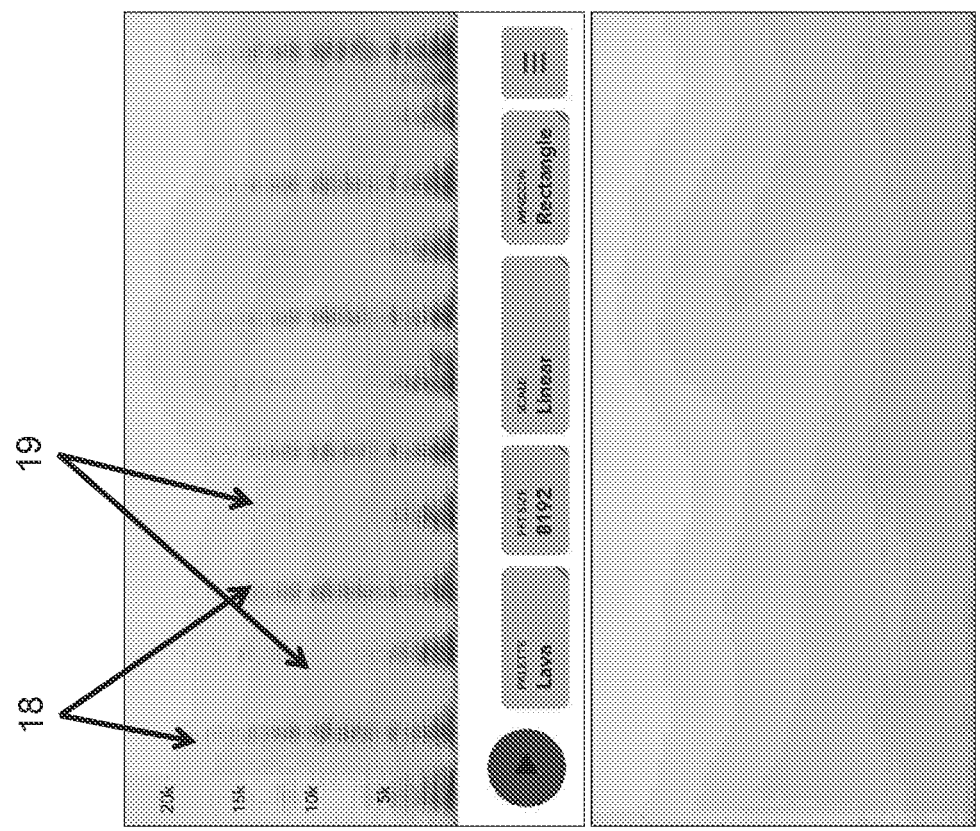
FIG. 16a shows an embodiment spectrum of the output signal of a microphone when placed at the location of the wearable for treating sleep apnea, and distinguishing features of this spectrum for inhaling vs. exhaling.
FIG. 16b shows the spectrum of FIG. 16a when breathing has stopped, simulating the conditions of a full obstruction of the airway.

FIG. 16a shows the frequency spectrum of the output of a microphone at the location of the wearable field generator 198 in FIG. 12b. This spectrum is derived from a Fast Fourier Transform of the time-domain waveform filtered by a rectangular filter, with 8192 frequency cells between 0 Hz and 20 KHz. The vertical axis is frequency and the horizontal axis is time, and both axes are linear in scale. The whiteness (color) at each point represents the signal strength for the given frequency at the given time. Differences exist between the spectral distribution during inhalation 18 vs. exhalation 19. Most notable is the lack of higher frequency content during exhalation 19 compared to inhalation. This spectral content signal could be used to detect the inhale portion of the breathing cycle to appropriately turn on and off the hypoglossal nerve stimulation to relieve obstructive sleep apnea. FIG. 16b shows the same spectrum when no breathing is occurring, as during a fully obstructive event or apnea. A spectrum in between that of FIG. 16a and FIG. 16b would be expected during a partially obstructive event or hypopnea.

Animal and Human Trials of Obstructive Sleep Apnea Prototype

Figure 17A:
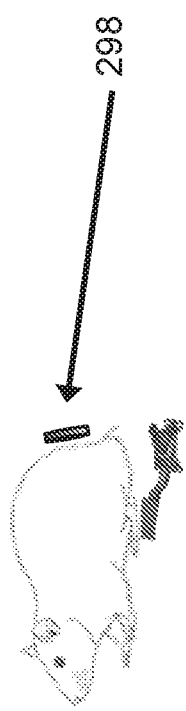
FIG. 17a shows the apparatus used for testing an embodiment neural stimulation in an animal trial involving a rat.
Figure 17B:
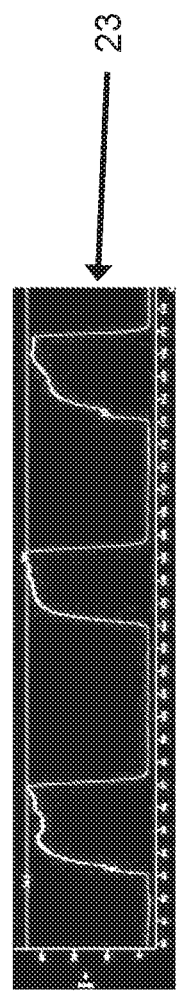
FIG. 17b shows the results of the experiment including measurements of the muscle force response from the stimulation.

FIG. 17a schematically depicts a rat that was anesthetized and the Injectable 199 of FIG. 1 was placed with stimulating electrode 4 adjacent to the sciatic nerve. After placement, the wound was stitched up. The rat, still anesthetized, was placed on a support apparatus that included a pedal transducer that measures the force from the rat's hind leg muscles. The wearable field generator 298 connected to an external pulse generator and external power supply, was mounted near the injectable location, and oriented orthogonally to the skin surface, similar to orientation 62 in FIG. 1. Then, pulse generator was turned on to 20 Hz with a burst width of 200 microseconds. When turned on, the muscle force 23 of FIG. 17b of the hind leg increased from zero to almost 40 grams, indicating a full recruitment of muscle response typical for this type of stimulation in a rat. The delay between the start of stimulation pulses and the appearance of muscle force was about 7 milliseconds, again an expected result as compared with wired stimulation.

In the first human experiment for obstructive sleep apnea, an interventional radiologist located the hypoglossal nerve in a human subject using a hand-held ultrasound imaging system 81 in FIG. 18a. The resulting image in FIG. 18b shows the hypoglossal nerve 82 about 1.1 centimeters below the surface, where the 1 cm depth line 83.

Figure 19A:
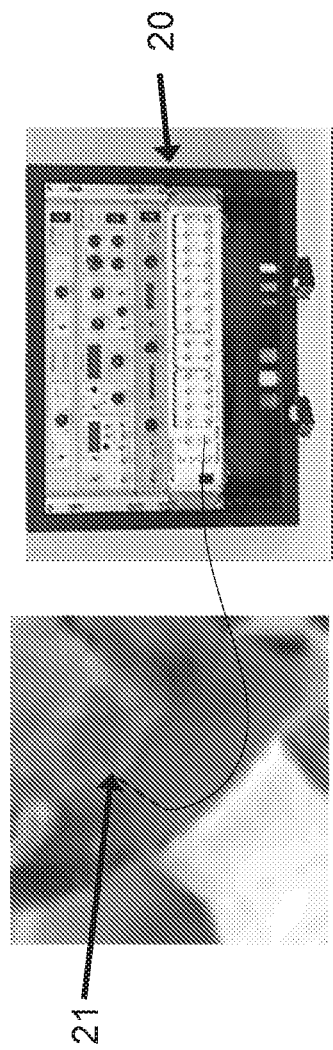
FIG. 19a shows the apparatus used to stimulate the hypoglossal nerve using prior-art wired stimulation to electrodes at the end of a needle connected to a lab instrument that is a pulse generator.
Figure 19B:
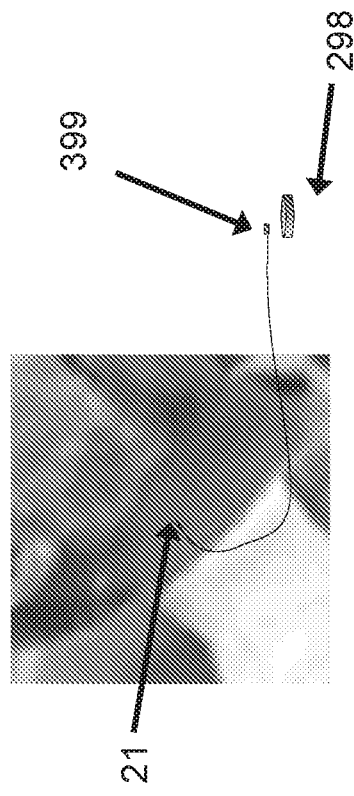
FIG. 19b shows an apparatus used to stimulate the hypoglossal nerve using an embodiments' wearable field generator and injectable, both located away from the body, but electrically connected to the intended locations of the electrodes inside the body if the injectable had been injected. The injectable and wearable parts of this embodiment are externally spaced apart and oriented as if they were located for treatment.

An experiment was conducted on a human subject as illustrated in FIG. 19a and FIG. 19b. Using the ultrasound imaging process described earlier, a needle 21 with two exposed electrodes about 0.5 cm apart was inserted into the neck until the deeper electrode, 1 mm long and 0.125 mm in diameter, was adjacent to the hypoglossal nerve in a human subject. The second shallow electrode, 2.5 mm long and 0.3 mm in diameter, was below the skin and served as a return electrode. First, as shown in FIG. 19a, the experiment was performed using a laboratory instrument 20 to generate neural stimulation pulses. The resulting movements of the subject's tongue were recorded and videotaped. Then, as schematically depicted in FIG. 19b, the leads to the needle electrode 21 were disconnected from the instrument 20 and connected to the injectable 399 of FIG. 8b, with the wearable field generator 298 in FIG. 19b separated from the injectable 2 by about 1.5 centimeters of air. Even though the injectable 399 was not actually injected into the body, this configuration in FIG. 19b represents an electrically equivalent apparatus as if the injectable were actually injected. The needle 21 electrodes were at the same locations as the two ends of the Injectable would be if injected. The air spacing between Injectable 399 and the wearable field generator 298 in FIG. 19b is representative of human tissue being therebetween, as magnetic fields are known to penetrate body tissue the same as air.

Figure 20B:
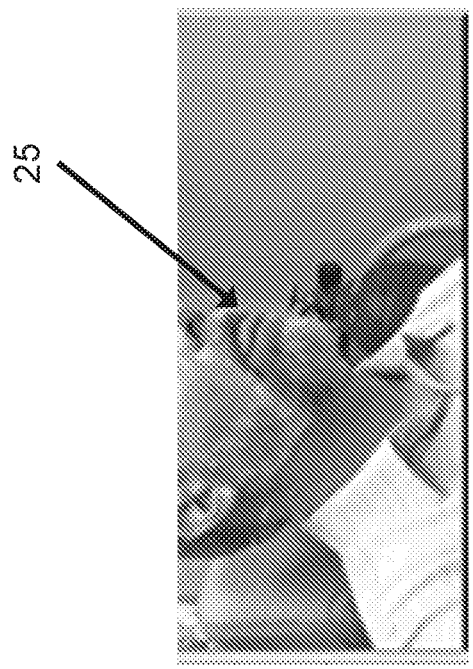
Figure 20A:
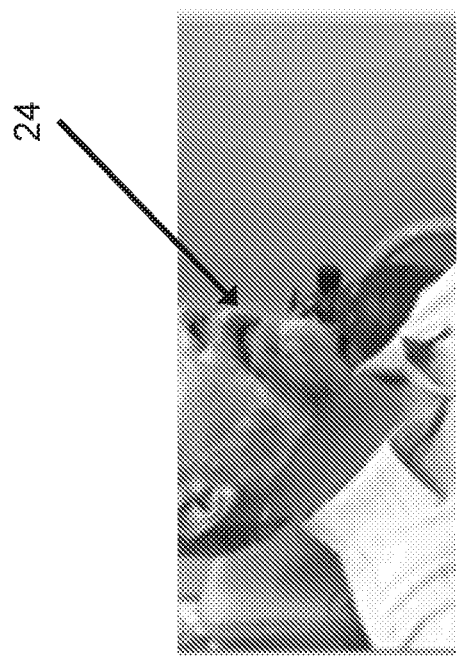
FIG. 20a shows the receding tongue position of a human subject using the apparatus of FIG. 19b with stimulation turned off.

FIG. 20a and FIG. 20b show the visible portion of the human subject's tongue during the experiment with the apparatus of FIG. 19b. When the stimulation is turned off, the tongue 24 is in a receding position. As the stimulation is turned on at 25 Hz and the amplitude increased gradually until a saturation effect was observed, the tongue is in a protruding position 25. In this experiment, the human subject reported no discomfort while awake and no interference with falling asleep. While in Stage 2 sleep a 4× reduction in obstructive events, hypopneas, was recorded by the attending scientist when the stimulation was turned on vs. turned off. A check of other muscle activity in this region of the body showed none, so no unintended collateral stimulation was occurring. Finally, no differences in systemic measurements, including heart rate, blood pressure, and oxygen saturation level were noted when stimulation was turned on vs. turned off.

FIG. 21a shows a treatment procedure for obstructive sleep apnea using an exemplary embodiment. First, the patient undergoes a sleep study. If the patient's Apnea-Hypopnea Index (AHI) is greater than 20 (obstructive events per hour), then he or she is considered for neural stimulation treatment. If the patient's neck circumference is greater than 36 inches, then the patient's airway likely has complete concentric collapse during apneas, in which case neural stimulation may not be effective. Once the patient is qualified, the attending physician locates the patient's hypoglossal nerve using ultrasound imaging as described earlier. The patient is prepped and draped in the usual sterile fashion. The depth of the nerve from the surface of the skin is identified in this step. Next, the injector with the injectable in the needle as illustrated in FIG. 2a is inserted into the patient to the target location and depth with the stimulating electrode brought to the nerve at a skin location where the skin surface is preferably orthogonal to target location, anatomy permitting. Then, the hypoglossal nerve is stimulated by the end of the needle connected to an instrumented pulse generator like the one in FIG. 19a. If the tongue muscles of the patient flex to open up the airway, then the attending physician pushes the plunger of the injector and simultaneously pulls out the injector to maintain the location of the injectable. Then, the injectable is fully committed to the body. Alternatively, the plunger of the injector may be held in place and the body of the injector and the needle is pulled back, so that the location of the injectable is not further displaced distally. In still further examples, implantation devices such as that taught in U.S. Pat. No. 8,540,681 may be used to reduce inadvertent displacement of the injectable once the desired target location is identified. In some examples, a lead of the test signal generator is attached to the needle by a clamp, with another lead attached to a skin electrode similar to an EKG pad, but in other examples, the injector and needle may be customized to include an electrical coupling located on the injector for one or both leads. The tissue tract formed by the needle may or may not require closure, which may be performed using a single stitch, skin adhesive or an adhesive bandage, surgical tape or a wound closure strip.

FIG. 21b shows and example of the remainder of the treatment procedure after the injectable is in place. First, the patient waits a period of 3, 7, 10, 14, 15, 21 or 30 days for the tissue surrounding the injectable to stabilize. During this time, the patient is instructed to not engage in any activities that involve sudden accelerator or deceleration of the head or neck. Then, the physician applies the wearable 298 in FIG. 2a, centered on the small scar left by the injection. The wearable and the base station 3 are configured for the appropriate level of stimulation. Then, the patient is taught how to use the device and discharged.

Although the present disclosure has been described in relation to various exemplary embodiments, various additional embodiments and alterations to the described embodiments are contemplated within the scope of the disclosure. Thus, no part of the foregoing description should be interpreted to limit the scope of the invention as set forth in the following claims. For all of the embodiments described above, the steps of the methods need not be performed sequentially.

I claim:

1. A neuromodulation system, comprising:
   at least one elongate device configured for implantation inside a body, the at least one elongate device comprising:
   a first and a second electrode;
   a diode electrically connected between the first and second electrodes, and wherein the diode is directly connected to the first electrode, wherein the diode is a silicon diode, Schottky diode, or a Zener diode; and
   at least one inductor, wherein the at least one inductor is directly connected to the diode and to the second electrode;
   wherein the at least one elongate device lacks a battery and a capacitor; and
   a magnetic field generator configured to be placed outside the body and generating a time varying magnetic field, wherein the magnetic field generator comprises:
   a coil;
   a capacitor connected in parallel with the coil, and together are configured to generate a stimulation signal that is a portion in time of a resonance between the parallel capacitor and coil;
   a DC power supply located at a first side of the parallel capacitor and coil, and configured to activate the parallel capacitor and coil;
   a switch to ground on a second side of the parallel capacitor and coil; and
   a microprocessor configured to turn off the switch just prior to a first series of decaying resonant pulses to provide a free running resonance between the coil and the capacitor and then turn on the switch to build up a current in the magnetic field generator prior to a second series of decaying resonant pulses, to reduce electrical energy in the coil between the first and second series of decaying resonant pulses.

2. The system of claim 1, wherein the diode is a Zener diode configured to limit a stimulation voltage to the first electrode to a safe level.

3. The system of claim 1, wherein the at least one elongate device is coated with at least one of a protective layer and an insulating layer.

4. The system of claim 3, wherein the protective layer comprises PTFE, nylon, silicone, polyethylene, polyurethane, latex, polyimide, BoPET, or any combination thereof.

5. The system of claim 1, wherein the at least one elongate device comprises an oblong shape with an oval side and having a diameter and a longitudinal length, wherein the diameter is less than the longitudinal length.

6. The system of claim 1, wherein the first electrode comprises an exposed wire, a plurality of exposed strands, or an exposed expandable mesh that is configured to expand in the body after injection.

7. The system of claim 1, wherein the coil of the magnetic field generator and the at least one inductor of the at least one elongate device comprises a ferromagnetic material with magnetic permeability between 1.1 and 10,000 configured to contain fringe fields.

8. The system of claim 7, wherein the ferromagnetic material comprises rigid or flexible ferrite, steel, or iron.

9. The system of claim 7, wherein the ferromagnetic material comprises iron, cobalt, nickel, steel, or an alloy or other combination thereof.

10. The system of claim 1, wherein the magnetic field generator comprises at least one of a plethysmography sensor, a blood oxygen level sensor, or a microphone.

11. The system of claim 10, wherein the magnetic field generator is configured to turn on stimulation during an inhalation phase of a breathing cycle of a patient and to turn off during an exhalation phase of the breathing cycle of the patient.

12. The system of claim 11, wherein the magnetic field generator is further configured to determine the phase of the breathing cycle using a change in an envelope of a plethysmography sensor output, a change in a frequency of the plethysmography sensor output, a change in a frequency spectral distribution of a microphone output, or a change in an amplitude of a blood oxygen sensor output, or a combination thereof.

13. The system of claim 12, wherein the change in the frequency spectral distribution of the microphone output is a presence or absence of high-frequency signal between the inhalation and exhalation phases.

14. The system of claim 11, further comprising a breathing sensor.

* * * * *